(12) United States Patent
Alam et al.

(10) Patent No.: US 12,044,669 B2
(45) Date of Patent: Jul. 23, 2024

(54) SYSTEM AND METHOD FOR DETECTING ANALYTES IN WATER

(71) Applicant: McMaster University, Hamilton (CA)

(72) Inventors: Arif Ui Alam, Hamilton (CA); Mohamed Jamal Deen, Dundas (CA)

(73) Assignees: McMaster University, Hamilton (CA); 2055218 Ontario Inc., Burlington (CA)

( * ) Notice: Subject to any disclaimer, the term of this patent is extended or adjusted under 35 U.S.C. 154(b) by 78 days.

(21) Appl. No.: 17/553,285

(22) Filed: Dec. 16, 2021

(65) Prior Publication Data

US 2022/0187269 A1 Jun. 16, 2022

Related U.S. Application Data

(60) Provisional application No. 63/126,218, filed on Dec. 16, 2020.

(51) Int. Cl.
| | |
|---|---|
| *G01N 27/30* | (2006.01) |
| *G01N 27/403* | (2006.01) |
| *G01N 33/18* | (2006.01) |

(52) U.S. Cl.
CPC ........... *G01N 33/18* (2013.01); *G01N 27/301* (2013.01); *G01N 27/302* (2013.01); *G01N 27/403* (2013.01)

(58) Field of Classification Search
CPC .... G01N 33/18; G01N 33/182; G01N 27/301; G01N 27/302; G01N 27/403; G01N 27/4166
See application file for complete search history.

(56) References Cited

U.S. PATENT DOCUMENTS

| | | | | |
|---|---|---|---|---|
| 4,680,268 A | * | 7/1987 | Clark, Jr. ............... | C12Q 1/005 600/347 |
| 4,781,798 A | * | 11/1988 | Gough ................. | G01N 27/404 600/382 |

(Continued)

FOREIGN PATENT DOCUMENTS

| | | | | |
|---|---|---|---|---|
| GB | 1431537 | * | 4/1976 | ............. G01N 27/50 |

OTHER PUBLICATIONS

Qin et al., "Microfabricated electrochemical pH and free chlorine sensors for water quality monitoring: recent advances and research challenges," RSC Adv., 2015, 5, 69086-69109 (Year: 2015).*

(Continued)

*Primary Examiner* — Alexander S Noguerola
(74) *Attorney, Agent, or Firm* — BERESKIN & PARR LLP/S.E.N.C.R.L., s.r.l.

(57) ABSTRACT

An electrochemical sensor array for detecting analytes in water, including a frame; a plurality of sensor electrodes each mounted to the frame, including a free chlorine working electrode including a gold thin film and having a free chlorine sensing surface to be exposed to the water; and a reference electrode including a silver thin film and a silver and silver chloride layer and having a reference sensing surface to be exposed to the water. A method of manufacturing an electrochemical sensor array for detecting analytes in water, including forming a free chlorine electrode, including forming a gold thin film on a first base layer; forming a reference electrode, including forming a silver thin film on a second base layer and applying a silver and silver chloride paste to a portion of the silver thin film; and arranging the free chlorine electrode and the reference electrode on a common frame.

18 Claims, 24 Drawing Sheets

(56) References Cited

U.S. PATENT DOCUMENTS

| | | | | |
|---|---|---|---|---|
| 5,437,999 | A * | 8/1995 | Diebold | G01N 27/3272 435/817 |
| 6,627,450 | B1 * | 9/2003 | Taylor | G01N 27/4168 436/125 |
| 8,142,641 | B2 | 3/2012 | Birch et al. | |
| 8,562,797 | B2 | 10/2013 | McCormack et al. | |
| 10,241,072 | B2 | 3/2019 | Rowhani et al. | |
| 2008/0047846 | A1 * | 2/2008 | Salzer | G01N 27/4168 204/426 |
| 2014/0083865 | A1 * | 3/2014 | Rowhani | G01N 27/403 205/782 |
| 2015/0177183 | A1 * | 6/2015 | Bakker | G01N 27/3335 204/295 |
| 2016/0047773 | A1 * | 2/2016 | Selvaganapathy | G01N 33/182 204/422 |
| 2016/0209346 | A1 * | 7/2016 | Brondum | G01N 27/4166 |
| 2018/0224390 | A1 | 8/2018 | Pan et al. | |

OTHER PUBLICATIONS

Qin et al., "Integrated water quality monitoring system with pH, free chlorine, and temperature sensors," Sensors Actuators B Chem., vol. 255, pp. 781-790, Feb. 2018, doi:10.1016/j.snb.2017.07.188).

Arif Ui Alam at el., (2021), A reusable, reagent-less free chlorine sensor using gold thin film electrode, The Analyst, 10.1039/D1AN00038A.

Guidelines for drinking-water quality, 3rd edition: vol. 1—Recommendations incorporating the first and second addenda (who.int). Dec. 2, 2008.

www.canada.ca/en/health-canada/services/publications/healthy-living/guidelines-canadian-drinkingwater-quality-chlorine-guidline-technical-document.html, "Guidelines for Canadian Drinking Water Quality: Guideline Technical Document—Chlorine—Canada.ca", 2009, assessed online Jan. 24, 2019.

Xu et al., "Real-time in situ sensing of multiple water quality related parameters using micro-electrode array (MEA) fabricated by inkjet-printing technology (IPT)", Sensors Actuators B Chem., vol. 237, pp. 1108-1119, Dec. 2016, doi: 10.1016/j.snb.2016.09.040.

Mross et al., "Integrated multi-sensor system for parallel in-situ monitoring of cell nutrients, metabolites, cell density and pH in biotechnological processes", Sensors Actuators B Chem., vol. 236, pp. 937-946, Nov. 2016, doi: 10.1016/j.snb.2016.03.086.

Kirsanov et al., "Indirect monitoring of protein A biosynthesis in E. coli using potentiometric multisensor system", Sensors Actuators B Chem., vol. 238, pp. 1159-1164, Jan. 2017, doi: 10.1016/j.snb.2016/j.snb.2016.02.073.

Banna et al., "Miniaturized water quality monitoring pH and conductivity sensors", Sensors Actuators B Chem., vol. 193, pp. 434-441, Mar. 2014, doi: 10.1016/j.snb.2013.12.002.

Zhou et al., "Fabrication of a Miniature Multi-Parameter Sensor Chip for Water Quality Assessment", Sensors, vol. 17, No. 12, p. 157, Jan. 2017, doi: 10.3390/s17010157.

Salazar et al., "Application of Prussian Blue electrodes for amperometric detection of free chlorine in water samples using flow injectinon analysis", Talanta, vol. 146, pp. 410-416, Jan. 2016, doi:10.1016/j.talanta.2015.08/072.

Liu et al., "Evaluation of Monochloramine and Free Chlorine Penetration in a Drinking Water Storage Tank Sediment Using Microelectrodes", Environ. Sci. Technol., vol. 53, No. 16, pp. 9352-9360, Aug. 2019, doi:10.1021/acs.est.9b01189.

Salazar et al., "A novel and improved surfactant-modified Prussian Blue electrode for amperometric detection of free chlorine in water", Sensors Actuators B Chem., vol. 213, pp. 116-123, Jul. 2015, doi:10.1016/j.snb.2015.02.092.

Olive-Monllau et al., "Flow injection analysis system based on amperometric thin-film transducers for free chlorine detection in swimming pool waters", Talanta, vol. 77, No. 5, pp. 1739-1744, Mar. 2009, doi:10.1016/j.talanta.2008.10.015.

Murata et al., "Electrochemical detection of free chlorine at highly boron-doped diamond electrodes", J. Electroanal. Chem., vol. 612, No. 1, pp. 29-36, Ja. 2008, doi:10.1016/j.jelechem.2007.09/006.

Dong et al., "Graphene Quantum Dot as a Green and Facile Sensor for Free Chlorine in Drinking Water", Anal. Chem., vol. 84, No. 19, pp. 8378-8382, Oct. 2012, doi:10.1021/ac301945z.

Munoz et al., "Modified multiwalled carbon nantube/epoxy amperometric nanocomposite sensors with CuO nanaparticles for electrocatalytic detection of free chlorine", Microchem. J., vol. 122, pp. 189-196, Sep. 2015, doi:10.1016/j.microc.2015.05.001.

Hsu et al., "A carbon nanotube based resettable sensor for measuring free chlorine in drinking water", Appl. Phys. Lett., vol. 106, No. 6, p. 063102, Feb. 2015, doi:10.1063/1.4907631.

Pan et al., "Low-Cost Graphite-Based Free Chlorine Sensor", Anal. Chem., vol. 87, No. 21, pp. 10734-10737, Nov. 2015, doi:10.1021/acs.analchem.5b03164.

* cited by examiner

SYSTEM AND METHOD FOR DETECTING ANALYTES IN WATER

CROSS REFERENCE TO RELATED APPLICATION

This application claims the benefit of U.S. Application No. 63/126,218 filed Dec. 16, 2020, the entire contents of which is incorporated herein by reference.

FIELD

The specification relates generally to sensors for monitoring water quality, and more specifically to a multi-sensor array for detecting analytes in water.

BACKGROUND

Water quality monitoring is important to preserve the safety of water resources for drinking, recreation, and consumer uses. Standard water quality parameters include free chlorine, total chlorine, pH, alkalinity, dissolved oxygen, and turbidity. Among these parameters, free chlorine, total chlorine, pH and alkalinity are important parameters in, for example, recreational water quality monitoring.

Free chlorine, the sum of hypochlorous acid and hypochlorite ion, is a widely used water disinfectant. Accurate monitoring of free chlorine concentration is used for drinking, recreational, and food processing water (see, G. F. Connell, The chlorination/chloramination handbook. American Water Works Association, 1996). According to The World Health Organization, free chlorine concentration in drinking water should be between 0.1-4 ppm (see, "WHO|Guidelines for drinking-water quality, 3rd edition: Volume 1—Recommendations," WHO, 2018, Accessed: Jan. 24, 2019. [Online]. Available: https://www.who.int/water_sanitation_health/publications/gdwq3rev/en/). On the other hand, the free chlorine concentration in a swimming pool should be between 1-3 ppm (see, "Guidelines for Canadian Drinking Water Quality: Guideline Technical Document—Chlorine—Canada.ca," 2009. Accessed: Jan. 24, 2019. [Online]. Available: https://www.canada.ca/en/health-canada/services/publications/healthy-living/guidelines-canadian-drinking-water-quality-chlorine-guideline-technical-document.html).

Conventional water quality monitoring systems may suffer from incomplete integration, may require sample collection and analysis by trained personnel, and/or may be expensive. Furthermore, these systems may measure only one parameter such as pH or free chlorine in a single measurement.

A standard method for measuring the free chlorine concentration requires the use of N,N'-diethyl-p-phenylenediamine (DPD). However, the DPD-based optical absorption method may not be user-friendly, may be prone to human error, and/or may be expensive. In addition, the DPD-based free chlorine reagent may contain ethylenedinitrilotetraacetic acid disodium salt dehydrate, which may be harmful to humans (see, Y. Qin et al., "Integrated water quality monitoring system with pH, free chlorine, and temperature sensors," Sensors Actuators B Chem., vol. 255, pp. 781-790, February 2018, doi:10.1016/j.snb.2017.07.188). Standard methods and/or apparatus for measuring total chlorine may also suffer from one or more issues similar to those for measuring free chlorine.

Conventional glass-based pH sensing electrodes may be bulky, fragile, and/or costly. These electrodes may not be user-friendly due, for example, to the need for frequent calibration and the requirement of complicated electronic circuits for signal conditioning. Total alkalinity, a measure of the pool water's buffering capacity, may also be an important parameter to be monitored. Conventional alkalinity measurement may follow titrimetric approaches which require the use harmful reagents.

Multi-sensor array-based sensing systems have been reported for monitoring dissolved oxygen, conductivity, temperature, pH, bacteria, and cell nutrients/metabolites (see, Z. Xu et al., "Real-time in situ sensing of multiple water quality related parameters using micro-electrode array (MEA) fabricated by inkjet-printing technology (IPT)," Sensors Actuators B Chem., vol. 237, pp. 1108-1119, December 2016, doi: 10.1016/j.snb.2016.09.040; S. Mross, T. Zimmermann, N. Winkin, M. Kraft, and H. Vogt, "Integrated multi-sensor system for parallel in-situ monitoring of cell nutrients, metabolites, cell density and pH in biotechnological processes," Sensors Actuators B Chem., vol. 236, pp. 937-946, November 2016, doi: 10.1016/j.snb.2016.03.086; D. Kirsanov, A. Korepanov, D. Dorovenko, E. Legin, and A. Legin, "Indirect monitoring of protein A biosynthesis in $E.coli$ using potentiometric multisensor system," Sensors Actuators B Chem., vol. 238, pp. 1159-1164, January 2017, doi: 10.1016/j.snb.2016.02.073; M. H. Banna, H. Najjaran, R. Sadiq, S. A. Imran, M. J. Rodriguez, and M. Hoorfar, "Miniaturized water quality monitoring pH and conductivity sensors," Sensors Actuators B Chem., vol. 193, pp. 434-441, March 2014, doi: 10.1016/j.snb.2013.12.002; B. Zhou, C. Bian, J. Tong, and S. Xia, "Fabrication of a Miniature Multi-Parameter Sensor Chip for Water Quality Assessment," Sensors, vol. 17, no. 12, p. 157, January 2017, doi: 10.3390/s17010157). Most of these studies focused on parameters involving human physiological conditions.

Patents related to electrochemical sensing systems have shown promises in water quality monitoring (see U.S. Pat. Nos. 8,142,641 B2; 8,562,797 B2; 10,241,072 B2; US 2018/0224390 A1).

Each document referred to herein is hereby incorporated by reference in its entirety.

SUMMARY

The following summary is intended to introduce the reader to various aspects of the applicant's teaching, but not to define any invention.

According to some aspects, there is provided an electrochemical sensor array for detecting analytes in water, comprising a frame; a plurality of sensor electrodes each mounted to the frame, including: a free chlorine working electrode including a gold thin film and having a free chlorine sensing surface to be exposed to the water; and a reference electrode including a silver thin film and a silver and silver chloride layer and having a reference sensing surface to be exposed to the water.

In some examples, the gold thin film includes a first end having the free chlorine sensing surface and a second end to be coupled to readout circuitry, with a passivation layer on the gold thin film between the first end and the second end.

In some examples, the passivation layer covers the gold thin film apart from the free chlorine sensing surface and a surface to be coupled to the readout circuitry.

In some examples, the reference sensing surface is a surface of the silver and silver chloride layer, and the silver and silver chloride layer is on a first end of the silver thin film and the silver thin film includes a second end to be coupled to readout circuitry, with a passivation layer on the silver thin film between the first end and the second end.

In some examples, the passivation layer covers the silver thin film apart from a first surface covered by the silver/silver chloride layer and a second surface to be coupled to the readout circuitry.

In some examples, the plurality of electrodes further comprises a total chlorine electrode including a carbon thin film and a total chlorine sensing reagent layer and having a total chlorine sensing surface to be exposed to the water, the total chlorine sensing reagent layer including amine-containing compounds and a binding polymer.

In some examples, the total chlorine sensing surface is a surface of the total chlorine sensing reagent layer, and the total chlorine sensing reagent layer is on a first end of the carbon thin film and the carbon thin film includes a second end to be coupled to readout circuitry, with a passivation layer on the carbon thin film between the first and second ends.

In some examples, the passivation layer covers the carbon thin film apart from a first surface covered by the total chlorine sensing reagent layer and a second surface to be coupled to the readout circuitry.

In some examples, the plurality of electrodes further comprises a pH electrode including a platinum and/or tantalum thin film and having a pH sensing surface to be exposed to the water.

In some examples, the pH sensing surface is a surface of an oxide layer of the platinum and/or tantalum thin film, and the oxide layer is on a first end of the platinum and/or tantalum thin film and the platinum and/or tantalum thin film includes a second end to be coupled to readout circuitry, with a passivation layer on the platinum and/or tantalum thin film between the first and second ends.

In some examples, the passivation layer covers the platinum and/or tantalum thin film apart from the oxide layer and a surface to be coupled to the readout circuitry.

In some examples, the plurality of electrodes further comprises an alkalinity electrode including a carbon thin film and an alkalinity sensing reagent layer and having a pH sensing surface to be exposed to the water, the alkalinity sensing reagent layer including manganese perchlorate and a binding polymer.

In some examples, the pH sensing surface is a surface of the alkalinity sensing reagent layer, and the pH sensing reagent layer is on a first end of the carbon thin film and the carbon thin film includes a second end to be coupled to readout circuitry, with a passivation layer on the carbon thin film between the first and second ends.

In some examples, the passivation layer covers the carbon thin film apart from a first surface covered by the alkalinity sensing reagent layer and a second surface to be coupled to the readout circuitry.

In some examples, the frame includes a common plate, and each of the plurality of electrodes is mounted to the common plate.

According to some aspects, there is provided a method of manufacturing an electrochemical sensor array for detecting analytes in water, comprising: forming a free chlorine electrode, including forming a gold thin film on a first base layer; forming a reference electrode, including forming a silver thin film on a second base layer and applying a silver and silver chloride paste to a portion of the silver thin film; and arranging the free chlorine electrode and the reference electrode on a common frame.

In some examples, arranging the free chlorine electrode and the reference electrode on a common frame includes removing one of the free chlorine electrode and the reference electrode from a second frame on which it was formed and transferring the one of the free chlorine electrode and the reference electrode to the common frame.

In some examples, removing the one of the free chlorine electrode and the reference electrode includes cutting the one of the free chlorine electrode and the reference electrode free of the second frame and transferring it to the common frame.

In some examples, forming the free chlorine electrode includes: arranging the first base layer on the common frame, applying a first chromium adhesion layer on the first base layer via a first sputtering process, applying the gold thin film on the chromium adhesion layer via a second sputtering process, and applying a first passivation layer to the gold thin film between a first end and a second end of the gold thin film; and forming the reference electrode includes: arranging the second base layer on the second frame, applying a second chromium adhesion layer on the second base layer via a third sputtering process, applying the silver thin film on the second chromium adhesion layer via a fourth sputtering process, and applying a second passivation layer to the silver thin film between a first end and a second end of the silver thin film, and applying the silver and silver chloride paste to the portion of the silver thin film at the first end.

According to some aspects there is provided a method of sensing free chlorine using an electrochemical sensor array, comprising: immersing the free chlorine electrode in the water; immersing the reference electrode in the water along with the free chlorine electrode; joining the free chlorine electrode and the reference electrode via readout circuitry, the readout circuitry including a potentiostat; applying 0 volts voltage potential difference between the free chlorine electrode and the reference electrode; measuring and recording the current response from the free chlorine electrode for a predetermined time while the free chlorine electrode and the reference electrode are immersed in the water; and comparing the current at the predetermined time with a pre-calculated calibration plot to measure the free chlorine concentration.

Other aspects and features will become apparent to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification and are not intended to limit the scope of what is taught in any way. In the drawings.

DETAILED DESCRIPTION

Figure 1:
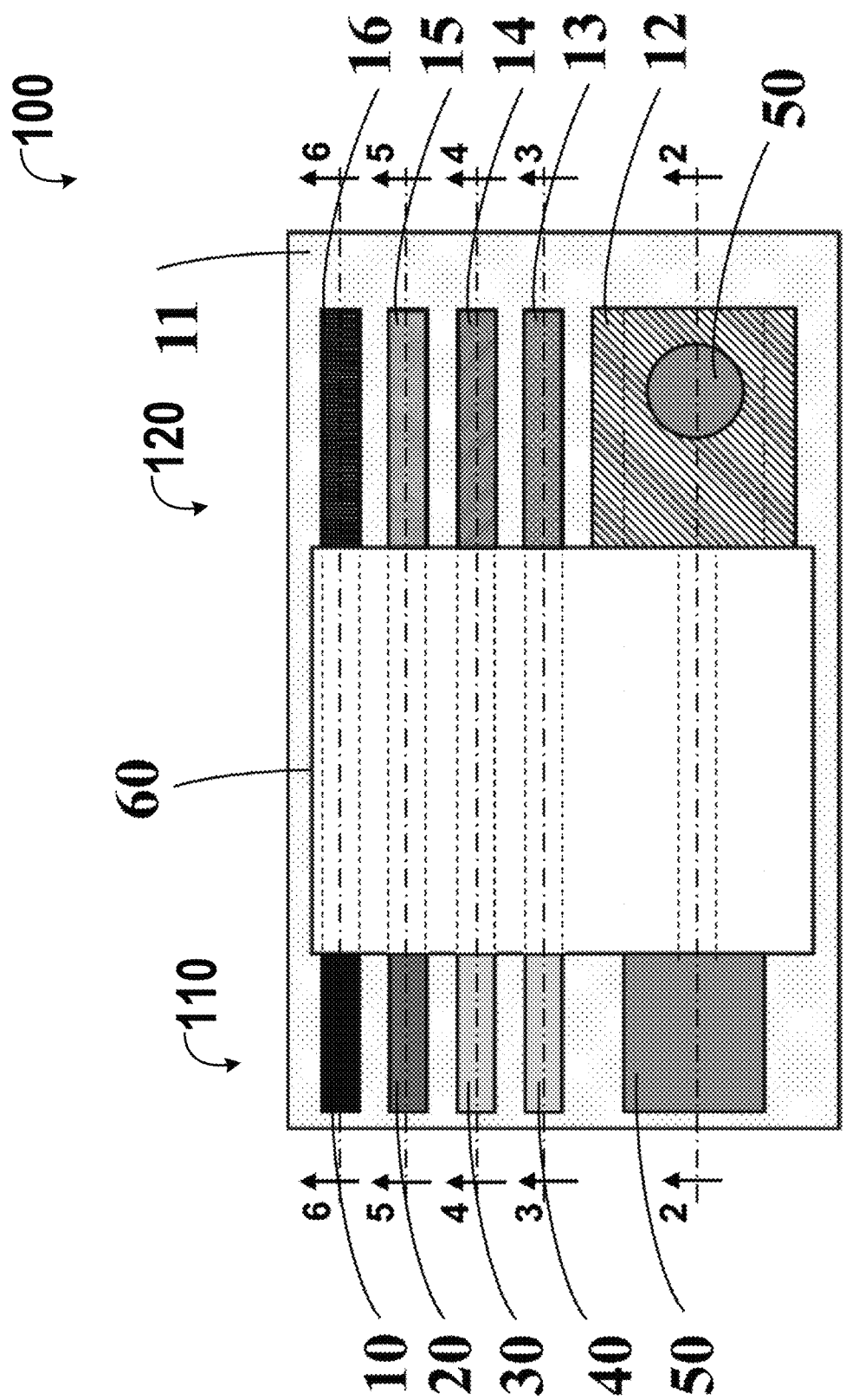
FIG. 1 shows the top view of a multi-sensor array.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim, or dedicate to the public any such invention by its disclosure in this document.

Some embodiments may provide a robust, reliable, low-cost, and portable free chlorine sensor for point-of-use sampling and/or analysis, which may increase public awareness and/or implement stricter public health regulations. Some embodiments may provide a multi-sensor array with high sensitivity, low-cost, high accuracy, reliability, and/or user-friendliness, such as for monitoring of critical water quality parameters to ensure water safety and/or maintain good public health. Some embodiments may provide a low-cost, integrated multi-sensor array to measure free chlorine, total chlorine, pH and alkalinity, such as for monitoring the quality of recreational water.

Some embodiments may utilize electrochemical sensing techniques, such as potentiometry and amperometry-based electrodes/sensors for monitoring of free chlorine, total chlorine, pH, and/or alkalinity (see P. Salazar, M. Martin, J. L. Gonzalez-Mora, and A. R. Gonzalez-Elipe, "Application of Prussian Blue electrodes for amperometric detection of free chlorine in water samples using flow injection analysis," Talanta, vol. 146, pp. 410-416, January 2016, doi: 10.1016/j.talanta.2015.08.072; H. Liu, D. G. Wahman, and J. G. Pressman, "Evaluation of Monochloramine and Free Chlorine Penetration in a Drinking Water Storage Tank Sediment Using Microelectrodes," Environ. Sci. Technol., vol. 53, no. 16, pp. 9352-9360, August 2019, doi: 10.1021/acs.est.9b01189). For example, some embodiments may make use of electrochemical reduction of hypochlorite ion in the working electrode. Working electrode materials for free chlorine sensing may include glassy carbon (see P. Salazar, M. Martin, F. J. Garcia-Garcia, J. L. Gonzalez-Mora, and A. R. Gonzalez-Elipe, "A novel and improved surfactant-modified Prussian Blue electrode for amperometric detection of free chlorine in water," Sensors Actuators B Chem., vol. 213, pp. 116-123, July 2015, doi: 10.1016/j.snb.2015.02.092), gold (see R. Olive-Monllau et al., "Flow injection analysis system based on amperometric thin-film transducers for free chlorine detection in swimming pool waters," Talanta, vol. 77, no. 5, pp. 1739-44, March 2009, doi: 10.1016/j.talanta.2008.10.015), boron-doped diamond (see M. Murata, T. a. Ivandini, M. Shibata, S. Nomura, A. Fujishima, and Y. Einaga, "Electrochemical detection of free chlorine at highly boron-doped diamond electrodes," J. Electroanal. Chem., vol. 612, no. 1, pp. 29-36, January 2008, doi: 10.1016/j.jelechem.2007.09.006), graphene (see Y. Dong, G. Li, N. Zhou, R. Wang, Y. Chi, and G. Chen, "Graphene Quantum Dot as a Green and Facile Sensor for Free Chlorine in Drinking Water," Anal. Chem., vol. 84, no. 19, pp. 8378-8382, October 2012, doi: 10.1021/ac301945z), carbon nanotubes (see J. Mufioz, F. Cespedes, and M. Baeza, "Modified multiwalled carbon nanotube/epoxy amperometric nanocomposite sensors with CuO nanoparticles for electrocatalytic detection of free chlorine," Microchem. J., vol. 122, pp. 189-196, September 2015, doi: 10.1016/j.microc.2015.05.001; L. H. H. Hsu, E. Hogue, P. Kruse, and P. Ravi Selvaganapathy, "A carbon nanotube based resettable sensor for measuring free chlorine in drinking water," Appl. Phys. Lett., vol. 106, no. 6, p. 063102, February 2015, doi: 10.1063/1.4907631), and potentially hazardous materials such as benzethonium chloride, and aniline oligomers.

Electrochemical sensing techniques may suffer from one or more issues. Free chlorine concentration may fluctuate, and the sensor performance may be deteriorated if there is hysteresis. A sensor may have difficulty distinguishing free chlorine from other interfering ions such as nitrates, sulfates, and bicarbonates, and chloride ions. An amperometric sensor may need frequent calibration due to poor stability of the sensing electrodes and/or degradation of the sensing materials. Some embodiments of the present disclosure use simple, robust and stable sensing materials, such as modified graphite, or gold (see S. Pan, M. J. Deen, and R. Ghosh, "Low-Cost Graphite-Based Free Chlorine Sensor," Anal. Chem., vol. 87, no. 21, pp. 10734-10737, November 2015, doi: 10.1021/acs.analchem.5b03164). However, modified graphite may be fragile and/or difficult to integrate on a two-dimensional substrate. Some embodiments of the present disclosure use gold. A gold-based electrode may be chemically stable with anything other than free chlorine at certain reduction potential, and may be easily mass fabricated. Some embodiments use a gold-based amperometric electrode that is not a microelectrode. In some embodiments, a gold-based amperometric electrode is used which does not require microfabrication techniques. Some embodiments may avoid additional challenges such as the use of flow-injection cell, high reduction potential, and difficulty in implementing on-site measurement.

Some embodiments utilize potentiometric sensors for pH sensing. Potentiometric sensors may have a compact structure, be miniaturizeable, be easy of fabrication, and/or be easy to integrate with other electrochemical sensors. Some embodiments utilize a potentiometric pH sensing electrode that is based on a metal oxide, such as platinum oxide, iridium oxide, ruthenium oxide, titanium oxide, and palladium oxide, and/or tantalum oxide. Some embodiments utilize platinum and/or tantalum due to, for example, higher pH sensitivity and/or long-term stability. Some embodiments utilize, a platinum and/or tantalum based potentiometric pH sensor capable of integration with other electrochemical sensors in an array format.

Some embodiments of the present disclosure include a multi-sensor electrochemical sensing system for simultaneous monitoring of free chlorine, total chlorine, pH, and alkalinity using gold, platinum/tantalum, silver and carbon-based electrodes. Some embodiments of the present disclosure include a multi-sensor electrochemical sensing system including a gold thin film based amperometric free chlorine sensor, a carbon/DPD-based amperometric total chlorine sensor, a platinum/tantalum based potentiometric free chlorine sensor, and a carbon/potassium permanganate-based amperometric alkalinity sensor, along with a silver/silver chloride reference electrode on a common substrate.

Some embodiments of the present disclosure include a reusable, reagent-less, free chlorine sensor using a gold thin film electrode. Some embodiments of the present disclosure include a fabrication approach. Some embodiments of the present disclosure include sensing method. Some embodiments of the present disclosure include a reference electrode and a free chlorine sensor. Some embodiments of the present disclosure include a total chlorine sensor, a pH sensor, and an alkalinity sensor along with a reference electrode and a free chlorine sensor.

Some embodiments of the present disclosure include an electrochemical sensor array for use in sensing free chlorine, total chlorine, pH and/or alkalinity in water samples. The electrochemical sensor array has a frame, which may be an insulating substrate. The electrochemical sensor array includes a plurality of electrodes on the frame. The electrodes may be arranged side by side. Each electrode may be electrically isolated from each other. In some embodiments, each electrode is fabricated separately on its own flexible, thermally stable substrate (for example, a polymeric substrate with adhesive backing) before being arranged together on a common frame (for example, the substrate of one or more electrodes being cut and transferred onto a common substrate).

In some embodiments, an (or each) electrode includes a first end forming the electrodes' electrical contact (such as for the readout circuitry) and a second end (optionally opposite the first end) at which a sensing surface is formed (such as for contact with water). The middle part of each electrode may be covered with a passivation layer (such as a polymeric passivation layer) to isolate unused sensor surfaces from electrical contact with liquid samples. The array of electrodes includes a free chlorine sensing electrode and a reference electrode, and may also include a total chlorine sensing electrode, a pH sensing electrode, and an alkalinity sensing electrode.

In some embodiments, a method of analyzing water parameters includes using a free chlorine electrode. The method may include using modified chronoamperometry that eliminates the use of a counter electrode due to applying 0 volts electrical potential bias between a working electrode and a reference electrode. The method may include measuring current response from chronoamperometry and using the current value at a predetermined time (such as at least 10 seconds, at least 20 seconds, at least 30 seconds, less than 120 seconds, less than 60 seconds, between 30 seconds and 60 seconds, and/or about 50 seconds). The method may be used for pH and temperature independent free chlorine sensing. In some embodiments, one or more processes or techniques are used as described by Arif Ul Alam at el., (2021), A reusable, reagent-less free chlorine sensor using gold thin film electrode, The Analyst, 10.1039/D1AN00038A.

Referring to FIG. 1, illustrated is a top view of an example multi-sensor array 100. The array 100 has a frame 110 to which a plurality of electrodes 120 are mounted.

In the illustrated example, the frame 110 includes a substrate 11. The illustrated substrate 11 is a plate and all electrodes are mounted to a common face of the plate, though it will be understood that the frame 110 may also or alternatively include other structural body members to hold the electrodes and/or the substrate 11 may be of other shapes with the electrodes otherwise arranged on the substrate. In the illustrated example, the substrate 11 is a microscope glass slide, though it will be understood that the frame 110 may include any electrically non-conductive and inert body.

The illustrated frame 110 has five electrodes mounted to the frame 110, though it will be understood that in some embodiments more or less electrodes may be used (such as for sampling more or less analytes in water, optionally with at least one electrode for each analyte to be sampled). The five electrodes include a free chlorine electrode 50, a reference electrode 40, a total chlorine electrode 30, a pH electrode 20, and an alkalinity electrode 10. In the illustrated example, the electrodes are electrically isolated from one another. In the illustrated example, the electrodes are well separated to avoid electrical connection between them.

One or more of the electrodes may include a base layer formed of a passivation material (such as to form, or be part of, a passivation layer on the electrode, optionally in addition to forming a flexible base to allow the electrode to be easily transferred). The base layers may be excluded in some embodiments, however in the illustrated example the base layers are included. The base layers (17a, 17b, etc.) may be portions of a common base layer, or may be distinct base layers (such as if an electrode is formed on a distinct substrate and then transferred along with the base layer to a common substrate, the base layer may assist in transferring the electrode). In other words, base layers 17a, 17b, etc. may be parts of the same base layer, or distinct base layers.

One or more of the electrodes may include a passivation layer formed on the electrode body (such as formed fully or partially of a tape). The passivation layer material may extend over several and/or all electrodes, or each electrode may be covered by distinct bodies of material. For example, the passivation layer may include the base layer (17a, 17b, etc.) under the electrode in connection with a sheet lying over the electrode (such as tape 60a, 60b, etc.). The sheet may be a single sheet lying over multiple electrodes, or multiple distinct sheets each lying over a single electrode or a subset of all the electrodes. In other words, tapes 60a, 60b, etc. may be parts of the same tape, or distinct tapes.

Optionally, one or more electrodes includes an additional layer, such as a layer to assist in manufacturing. For example, one or more electrodes may include an adhesion layer between the base layer and the electrode body.

In the illustrated example, for each electrode, a first end of the electrode is used for electrical contact with a readout circuit (such as an external readout circuit) and the other end is used for sensing, while a middle portion is covered with a passivation layer 60. Illustrated in FIGS. 2-6 are cross sectional views taken along the section lines 2-2, 3-3, 4-4, 5-5 and 6-6, these show the exaggerated cross-sectional side views of the free chlorine electrode, the reference electrode, the total chlorine electrode, the pH electrode, and the alkalinity electrode, respectively.

Figure 2:
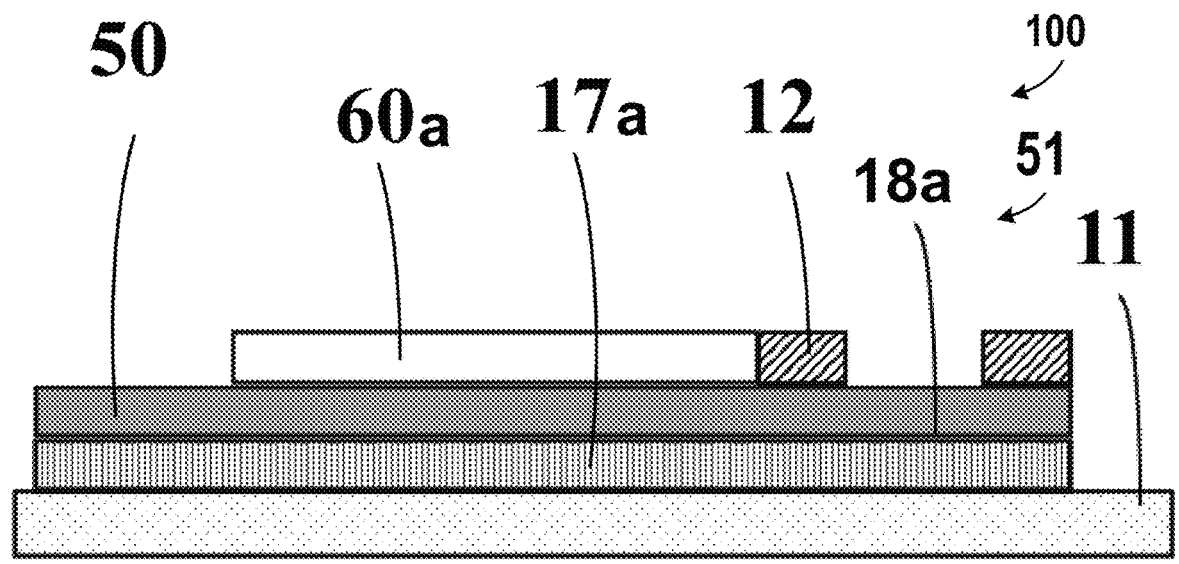
FIG. 2 shows an exaggerated cross-sectional view of the array of FIG. 1, taken along line 2-2.

Illustrated in FIG. 2 is an exaggerated cross-sectional side view of the free chlorine sensing electrode 50 taken along the section line 2-2. A free chlorine electrode assembly 51 includes a base layer 17a. The base layer 17 may be a thin adhesive film, such as made of Kapton™ polyimide. The example free chlorine electrode assembly 51 includes a gold thin film 50 (which may also be referred to as an electrode or electrode body) formed on the base layer 17a.

In some embodiments, the gold thin film 50 is made of ~300 nm of gold. In some embodiments, the thin film 50 was deposited through magnetron sputtering. For example, a method of forming the electrode 50 may include taking a substrate (such as a microscope glass slide), covering the substrate with the base layer (such as polyimide tape), cleaning the substrate covered with the base layer (such as cleaning with alcohol and DI (deionized) water and drying, such as drying on a hotplate). The method may include placing the substrate with the base layer in a sputtering chamber, depositing an adhesion layer 18a (such as approximately 50 nm of chromium adhesion layer), such as using a direct current (DC) sputtering power of 100 W, chamber Ar gas pressure of 5 mtorr and substrate rotation of 10 rpm. The method includes depositing a gold thin film 50 (such as approximately 300 nm of gold), such as using a radio frequency (RF) sputtering power of 200 W, chamber Ar gas pressure of 5 mtorr and substrate rotation of 10 rpm. The method may include attaching a Styrofoam adhesive tape 12 to the end of the gold film 50 so that only a sensing area (for example a punched area surrounded by tape 12; such as an area of between 0.1 and 10, 0.25 and 1, 0.25 and 0.5, or about 0.36 square centimeters) is exposed to the solution under test. The method may include covering the thin film with a passivation layer, such as by coving the gold thin film between the ends with another polyimide tape 60a which worked as the passivation layer over that portion of the gold thin film. In some embodiments, the free chlorine electrode (the gold thin film electrode) is resized (such as cut down), such as to a total area of the gold thin film of 8 mm×70 mm (for example, so that the substrate can accommodate the other electrodes).

Referring again to FIG. 1, a reference electrode (such as a silver and silver chloride electrode) may be arranged on the frame (such as hand-drawn beside the free chlorine electrode).

Figure 3:
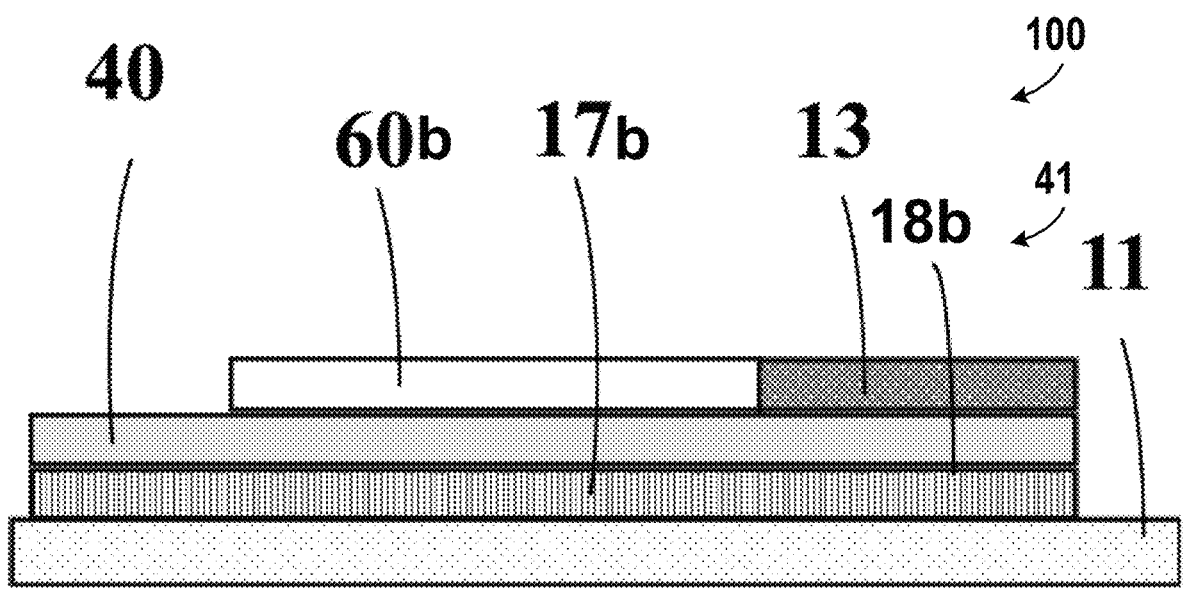
FIG. 3 shows an exaggerated cross-sectional view of the array of FIG. 1, taken along line 3-3.

Referring now to FIG. 3, illustrated is an exaggerated cross-sectional side view of the reference electrode along the section line 3-3. The reference electrode assembly 41 includes a base layer 17b. The base layer may be the same base layer as extends into the free chloride electrode assembly, or a distinct base layer. In the illustrated example, the base layer is a thin adhesive film 17b (such as made of Kapton™ polyimide).

The exemplary reference electrode assembly 41 includes a silver thin film 40 (which may also be referred to as an electrode or electrode body) formed on the base layer 17b. The example thin film 40 is made of ~300 nm of silver. In some embodiments, the thin film 40 was deposited through magnetron sputtering. For example, a method of forming the electrode 40 may include covering a substrate (the same substrate as the electrode 50 was formed on or a distinct substrate), such as a microscope glass slide, with the base layer (the same base layer as the electrode 50 was formed on or a distinct base layer 17b), such as with a layer of polyimide adhesive tape. The method may include cleaning the substrate and base layer, such as cleaning with alcohol and DI water and drying on a hotplate. The cleaned substrate and base layer may then be placed in a radio frequency (RF) sputtering chamber. The method may then include forming an adhesion layer on the base layer (such as approximately 50 nm of chromium adhesion layer), such as deposited using DC sputtering power of 100 W, chamber Ar gas pressure of 5 mtorr and substrate rotation of 10 rpm. The method may also include forming the thin film 40 on the substrate (such as on the adhesion layer 18b), such as depositing approximately 300 nm of silver using RF sputtering with a power of 200 W, chamber Ar gas pressure of 5 mtorr and substrate rotation of 10 rpm. The method may also include covering the thin film 40 with a passivation layer, such as by covering the silver thin film between the ends with another polyimide tape 60b which worked as the passivation layer. The method may also include, (such as, after applying the passivation layer) applying a silver and silver chloride (Ag/AgCl) reference electrode paste 13 on the end of the silver film (such as by hand-drawing or screen printing). The method may then include sintering the paste (such as at 120° C. for 30 minutes). In some embodiments, the reference electrode 40 is resized (such as cut down), such as to a total area of the silver electrode 40 of 8 mm×70 mm.

In some embodiments, the reference electrode 40 is formed on a substrate that is distinct from the substrate on which the free chlorine electrode was formed. The reference electrode may be transferred to another substrate (the substrate on which the free chlorine electrode was formed or another substrate to which the free chlorine electrode is also transferred). The base layer(s) 17a and/or 17b may be flexible films, such as flexible polyimide adhesive films, which may allow them to be highly manufacturable and with subsequent easy transfer of these electrodes on another substrate for integration. The use of polyimide film may allow high chemical and mechanical stability of the films. The use of polyimide film may allow the metal films to be heated up to a moderate temperature of 200 to 300° C. without causing any degradation or modification of the film/base layer interface.

Figure 4:
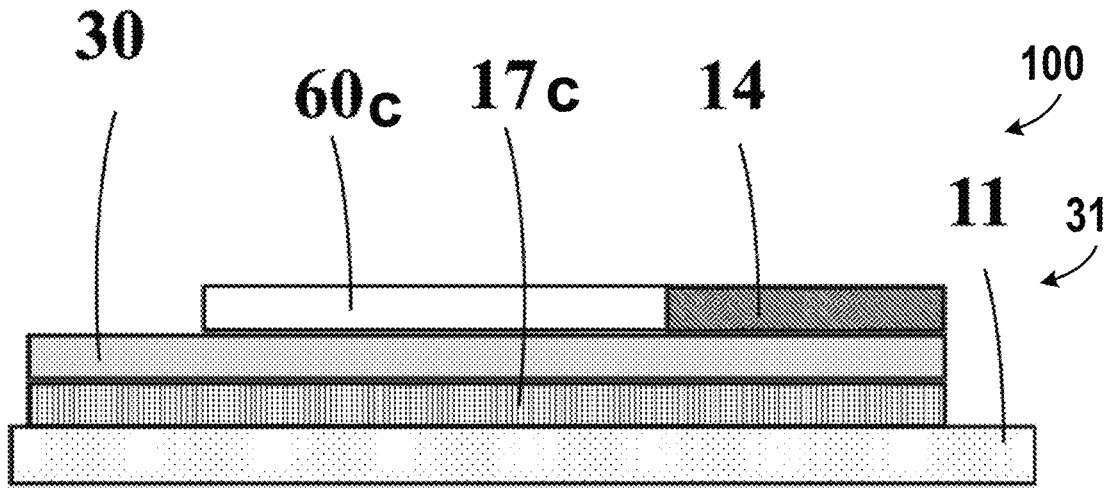
FIG. 4 shows an exaggerated cross-sectional view of the array of FIG. 1, taken along line 4-4.

Referring now to FIG. 4, illustrated is an exaggerated cross-sectional side view of a total chlorine sensing electrode assembly 31 along the section line 4-4. The assembly 31 includes a base layer 17c, such as a thin adhesive film (such as made of Kapton polyimide), which may be the same as layer 17a and/or 17b or distinct from layer 17a and layer 17b. The assembly 31 also includes a carbon-based thin film 30 (which may also be referred to as an electrode or electrode body) formed on the base layer 17c. For example, a method may include forming a thin film of carbon paste (such as through drop-casting or screen printing) on the base layer 17c. The method may include sintering the thin film of carbon paste (such as in a hotplate at 60° C. for 30 minutes) to form the thin film 30. The method may then include covering the thin film 30 with a passivation layer (for example, the middle part of the carbon electrode 30 may be covered with polyimide tape 60c which will work as the passivation layer). The method may include applying a total chlorine sensing reagent 14 (such as containing a mixture of amine-containing compounds and another binding polymer) to the thin film 30, such as via drop-casting and heating the reagent 14 (such as heating at 100° C. on a hotplate for 15 minutes). The electrode 30 may be resized (such as cut down), such as to a total area of 8 mm×70 mm.

In some embodiments, the electrode 30 is formed on a substrate that is distinct from the substrate on which the electrode 50 and/or electrode 40 is formed. The electrode 30 may be transferred to another substrate (the substrate on which one or more other electrode was formed or another substrate to which the other electrodes are also transferred). The base layer may be a flexible film, such as a flexible polyimide adhesive film.

Figure 5:
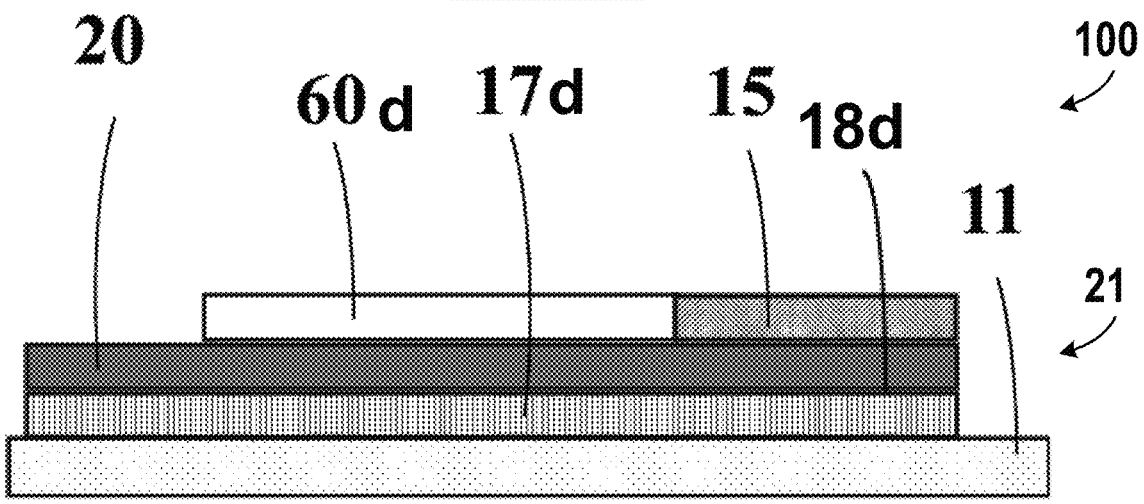
FIG. 5 shows an exaggerated cross-sectional view of the array of FIG. 1, taken along line 5-5.

Referring now to FIG. 5, illustrated is an exaggerated cross-sectional side view of a pH electrode assembly 21 along the section line 5-5. The assembly 21 includes a base layer 17d (such as a thin adhesive film made of Kapton polyimide). The assembly 21 includes a platinum and/or tantalum thin film 20 (which may also be referred to as an electrode or electrode body) formed on the base layer 17d. For example, a method may include depositing a thin film of platinum and/or tantalum (such as ~300 nm of platinum and/or tantalum), such as using magnetron sputtering. The method may include covering a substrate (such as a microscope glass slide) with the base layer 17d (such as polyimide adhesive tape). The substrate with the base layer 17d may be cleaned (such as cleaned with alcohol and DI water and dried on a hotplate). The method may include placing the substrate and base layer 17d in an RF sputtering chamber and depositing an adhesion layer 18d (such as approximately 50 nm of chromium adhesion layer), such as using a DC sputtering power of 100 W, chamber Ar gas pressure of 5 mtorr and substrate rotation of 10 rpm. The method may then include depositing a thin film 20 on the adhesion layer 18d (such as approximately 300 nm of platinum and/or tantalum), such as using radio frequency (RF) sputtering power of 200 W, chamber Ar gas pressure of 5 mtorr and substrate rotation of 10 rpm. The method may include, covering the thin film 20 with a passivation layer (such as covering a middle part of the platinum and/or tantalum electrode film 20 with another polyimide tape 60d which will work as the passivation layer). The method may include forming an oxide layer 15 on the platinum and/or tantalum electrode, such as by heating the film 20 (such as heating at 200° C. on a hotplate for 30 minutes). The platinum and/or tantalum oxide layer generated may form the sensing surface, and may work as the potentiometric pH sensor. The pH electrode 20 may be resized (such as cut down), such as to a total area of 8 mm×70 mm.

In some embodiments, the electrode 20 is formed on a substrate that is distinct from the substrate on which the electrode 50, electrode 40, and/or electrode 30 is formed. The electrode 20 may be transferred to another substrate (the substrate on which one or more other electrode was formed or another substrate to which the other electrodes are also transferred). The base layer may be a flexible film, such as a flexible polyimide adhesive film.

Figure 6:
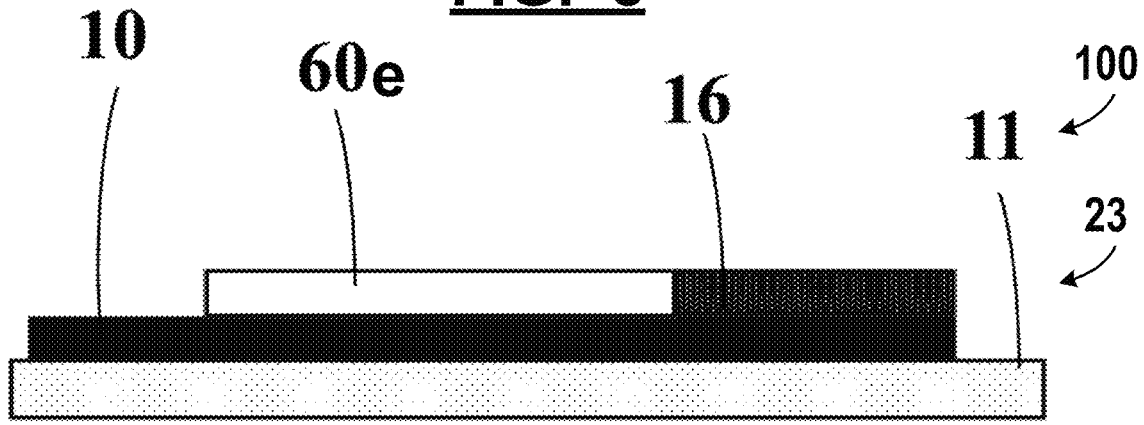
FIG. 6 shows an exaggerated cross-sectional view of the array of FIG. 1, taken along line 6-6.

Referring to FIG. 6, illustrated is an exaggerated cross-sectional side view of an alkalinity electrode assembly 23 along the section line 6-6. The assembly 23 may include a base layer (such as a thin adhesive film, such as made of Kapton polyimide) between the thin film 10 (which may also be referred to as an electrode or electrode body) and the substrate 11, although the illustrated assembly 23 is shown without the base layer. The assembly 23 includes a carbon-based thin film 10 formed on the substrate 11 (or base layer if a base layer is included). A method may include forming a thin film of carbon paste on the base layer or substrate, such as using drop-casting or screen printing. The method then includes sintering the carbon paste (such as in a hotplate at 60° C. for 30 minutes). The method may include applying a passivation layer, such as covering the thin film 10 with a passivation layer (for example, over the middle part of the electrode), such as a polyimide tape 60e which will work as the passivation layer. The method also includes applying an alkalinity sensing reagent 16 (such as containing a mixture of manganese perchlorate and another binding polymer), such as using drop-casting and heating (such as at 100° C. on a hotplate for 15 minutes). The electrode 10 may be resized (such as cut down), such as to a total area of 8 mm×70 mm.

In some embodiments, the electrode 10 is formed on a substrate that is distinct from the substrate on which the electrode 50, electrode 40, electrode 30 and/or electrode 20 is formed. The electrode 10 may be transferred to another substrate (the substrate on which one or more other electrode was formed or another substrate to which the other electrodes are also transferred). The base layer may be a flexible film, such as a flexible polyimide adhesive film.

Figure 7A:
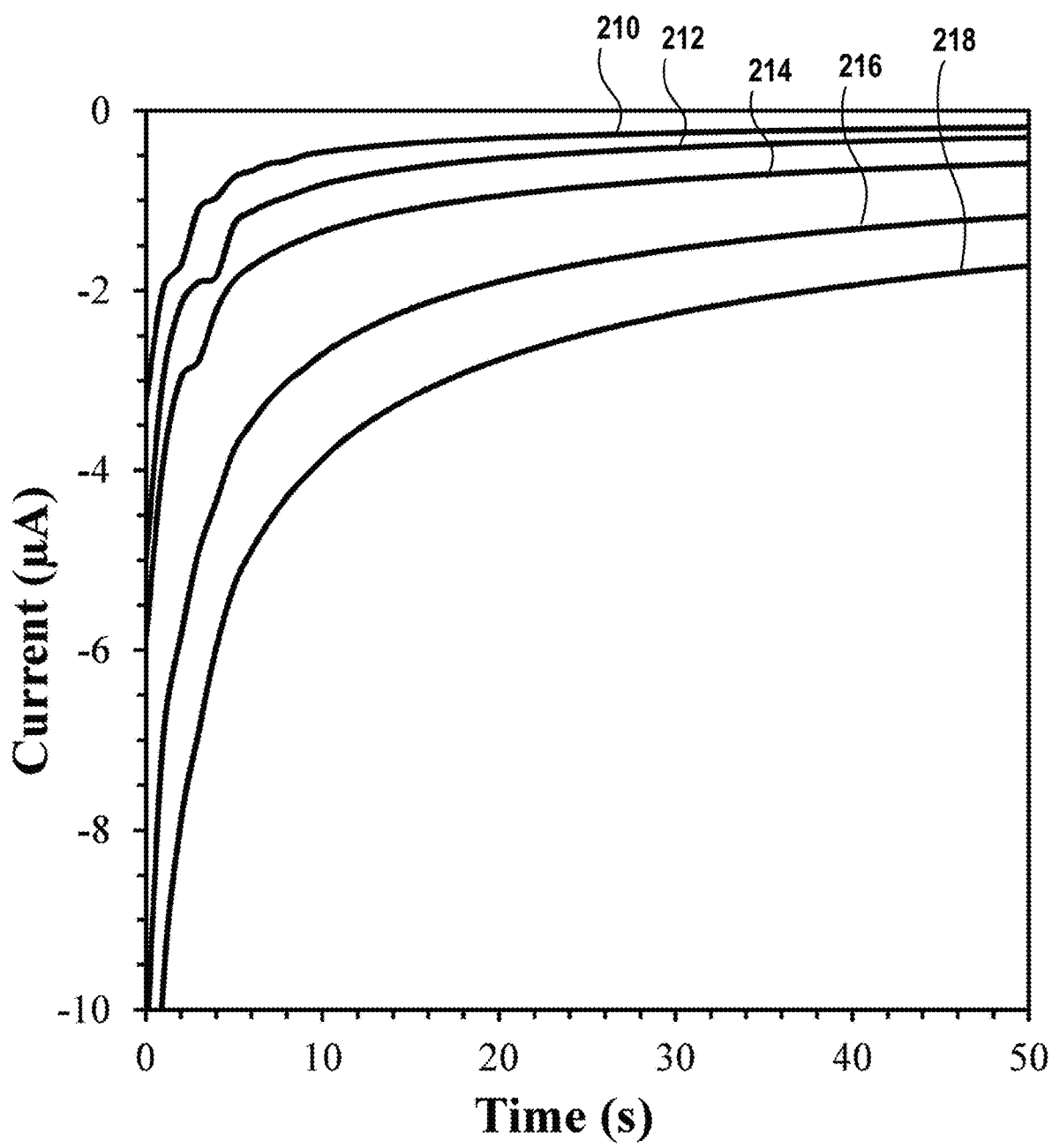
FIG. 7A is a graph of the chronoamperometric response to increasing free chlorine concentration from 0.8 ppm to 5.5 ppm.
Figure 7B:
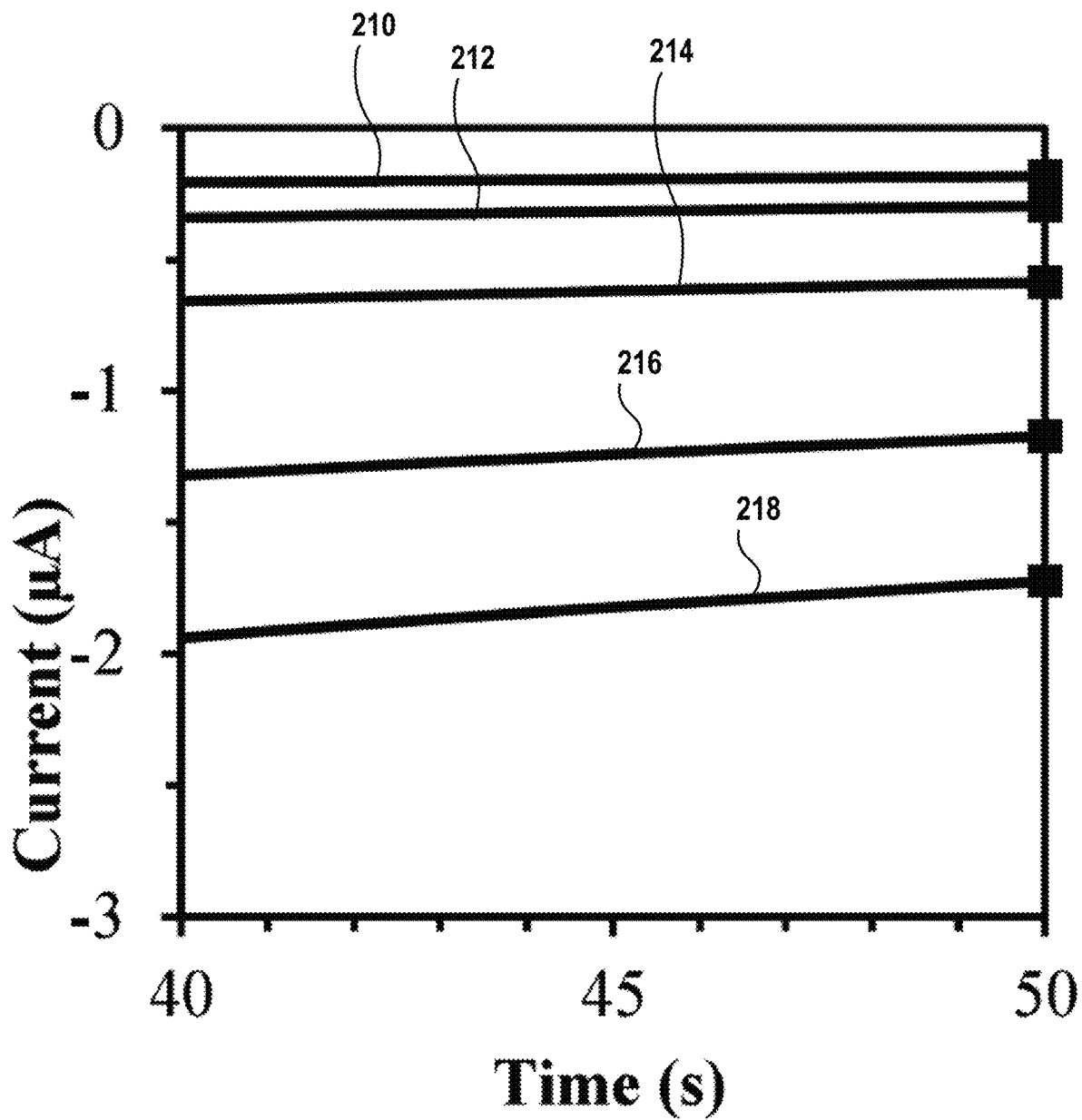
FIG. 7B is an expanded view of a portion of FIG. 7A.
Figure 7C:
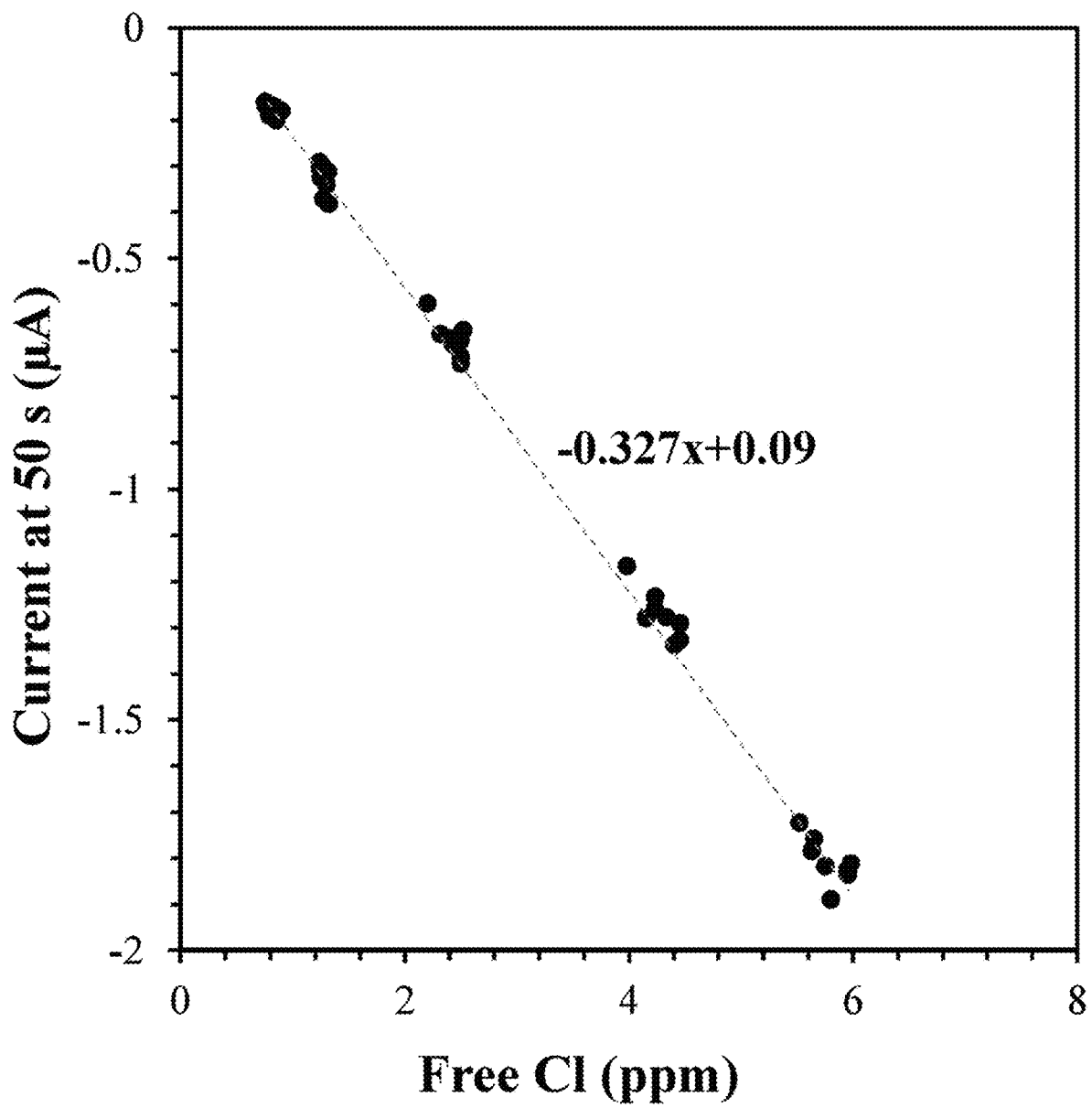
FIG. 7C is a calibration graph derived from the chronoamperometric response to free chlorine concentrations.

Referring to FIGS. 7A to 7C, illustrated is experimental results. Illustrated is the chronoamperometric response to increasing free chlorine concentration from 0.8 ppm to 5.5 ppm, using an example array similar to array 100 of FIG. 1.

Illustrated are plots for 0.8 ppm 210, 1.2 ppm 212, 2.2 ppm 214, 4 ppm 216, and 5.5 ppm 218. Different concentrations of free chlorine stock solutions were prepared by diluting the as-received NaOCl using a 0.01 M PBS solution at pH=7.4. The prepared solutions were calibrated using LaMotte 2056 ColorQ PRO 7 Hand-Held Photometer, a commercial DPD-based colorimetric test kit. The free chlorine sensor was characterized by a simplified amperometric configuration, where the gold thin film was used as the working electrodes and Ag/AgCl film as the reference/counter electrode. A potentiostat readout device connected to a laptop was used to measure the current flowing through the working and the reference/counter electrodes. The current measurement was done 1× per second (1 Hz) for 50 s when the electrodes were dipped into free chlorine solutions without stirring. The sensor was transferred into the next free chlorine solution without further cleaning or drying. The free chlorine sensing performance was characterized by a simplified amperometry. In this method, the Ag/AgCl worked as both the reference and counter electrode, resulting in a reduction potential of 0 V. The HOCl undergoes electrochemical reduction at the working electrode according to the following equation:

$$HOCl + 2e^- \rightarrow Cl^- + OH^- \tag{1}$$

The resulting output current is proportional to the HOCl concentration. This method eliminates the use of any external power supply (i.e., potentiostat) to activate the sensor. This may simplify the sensing method by avoiding the complexity of a conventional 3 electrodes-based and potentiostat-controlled amperometry and reducing the number of electrodes from three to two. The output current of the sensor started to settle after an initial impulse depending on the free chlorine concentration of the water sample. As shown in FIG. 7A, the total response time of the free chlorine sensor was selected to be 50 s, which is suitable for on-site monitoring. The output current value at 50th second, as shown in FIG. 7B, was used for the calibration measurement.

FIG. 7C shows the sensitivities of 3 free chlorine sensors that were fabricated in the same batch. The average sensitivity was 0.327 µA/ppm (0.9 µA/mm2/ppm for the sensors with an electrode area of 36 mm2). The sensitivity variation was only ±0.014 µA/ppm (0.00038 µA/mm2/ppm, 4% of the sensitivity). This variation corresponds to an accuracy of ±0.05 ppm. Therefore, the sensors showed high reproducibility with a negligible sensor-to-sensor variation of the output current at a certain free chlorine concentration with high sensitivity. The high reproducibility of the sensor helped to develop an easy-to-use sensing system since the calibration information was stored in the electronic system just once, after which, the calibration measurement was not needed to be performed before each measurement.

Figure 8A:
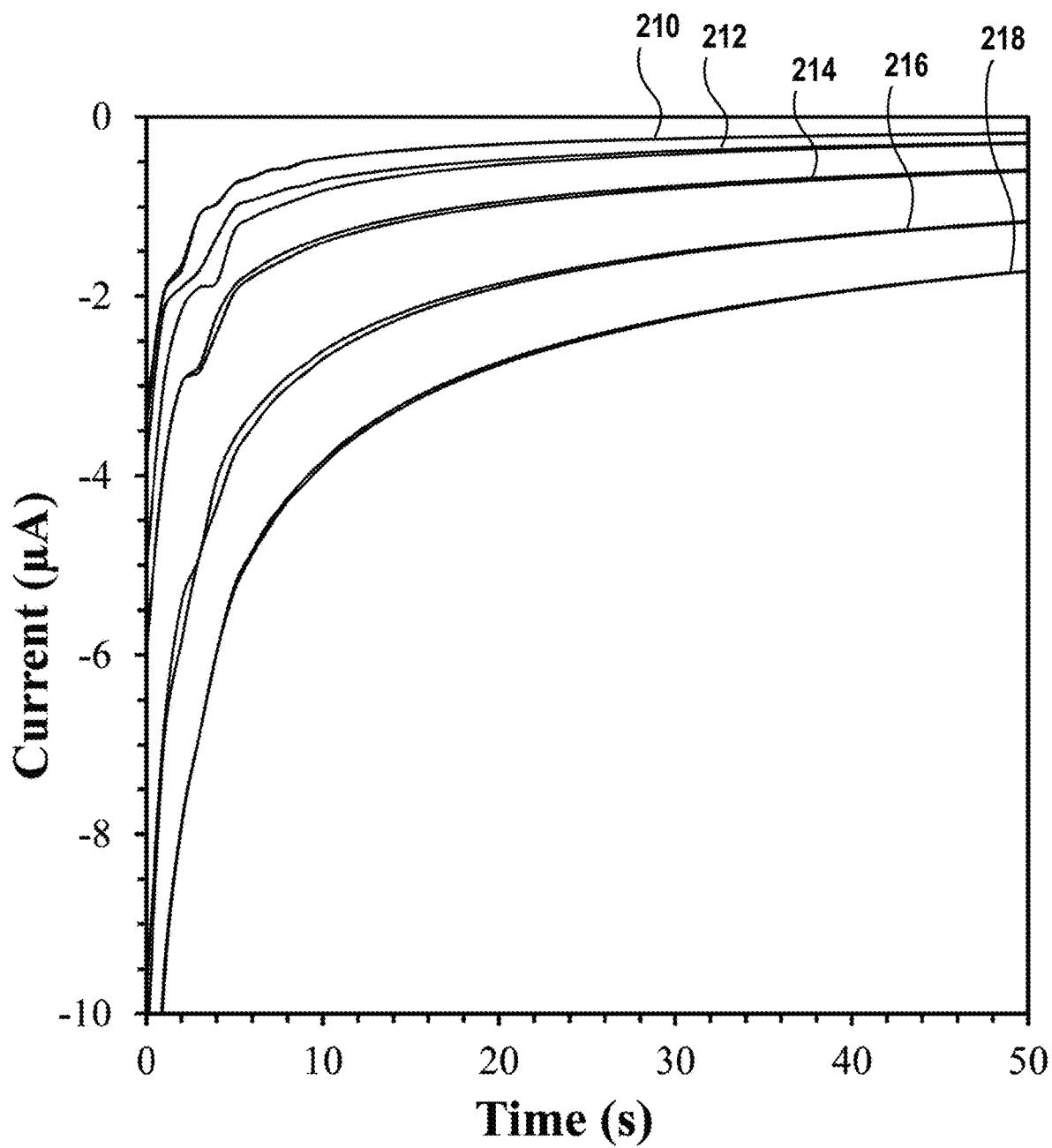
FIG. 8A is a graph of the chronoamperometric response to increasing (0.8 ppm to 5.5 ppm) and decreasing (5.5 ppm to 0.8 ppm) free chlorine concentrations.
Figure 8B:
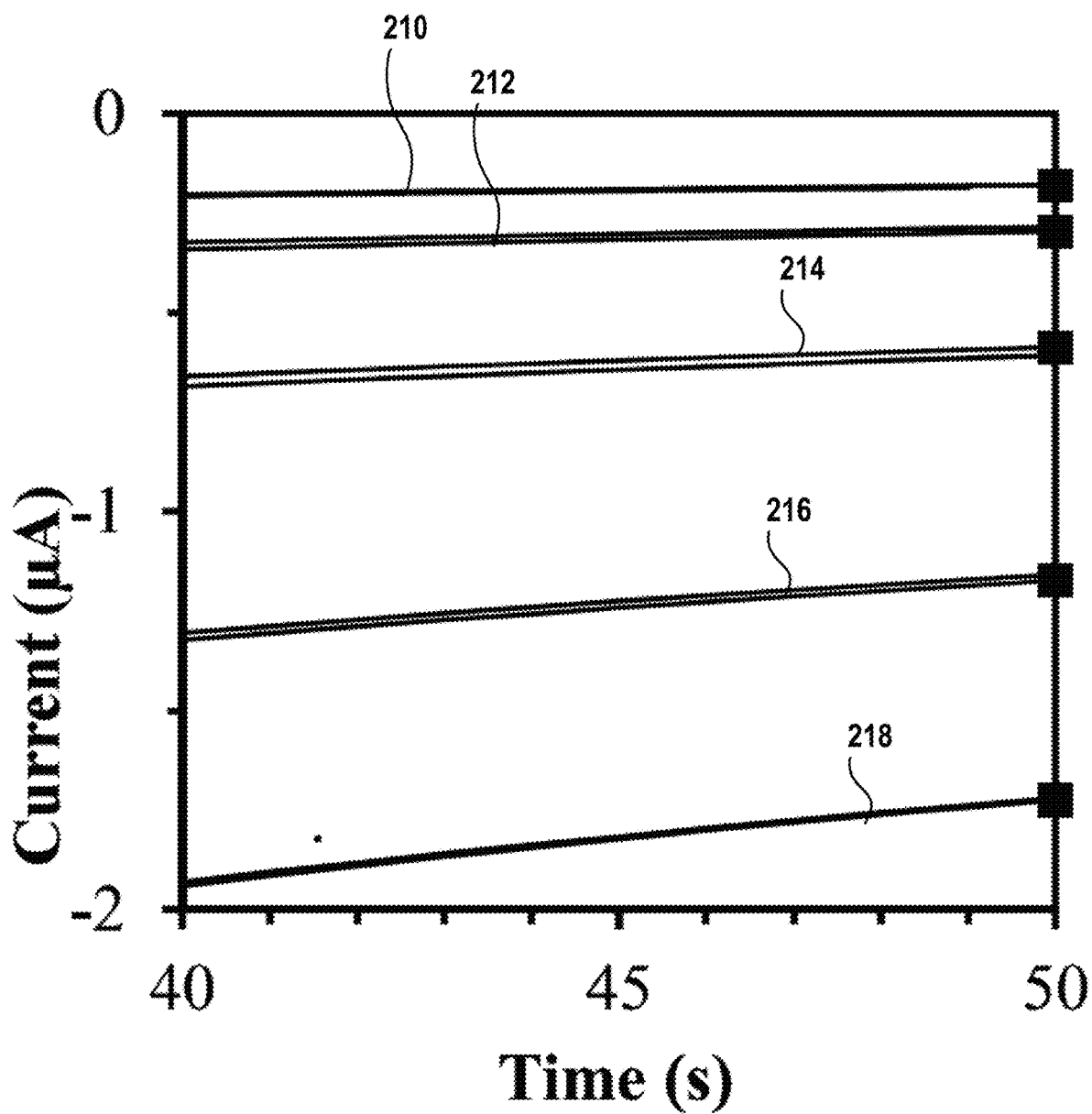
FIG. 8B is an expanded view of a portion of FIG. 8A.
Figure 8C:
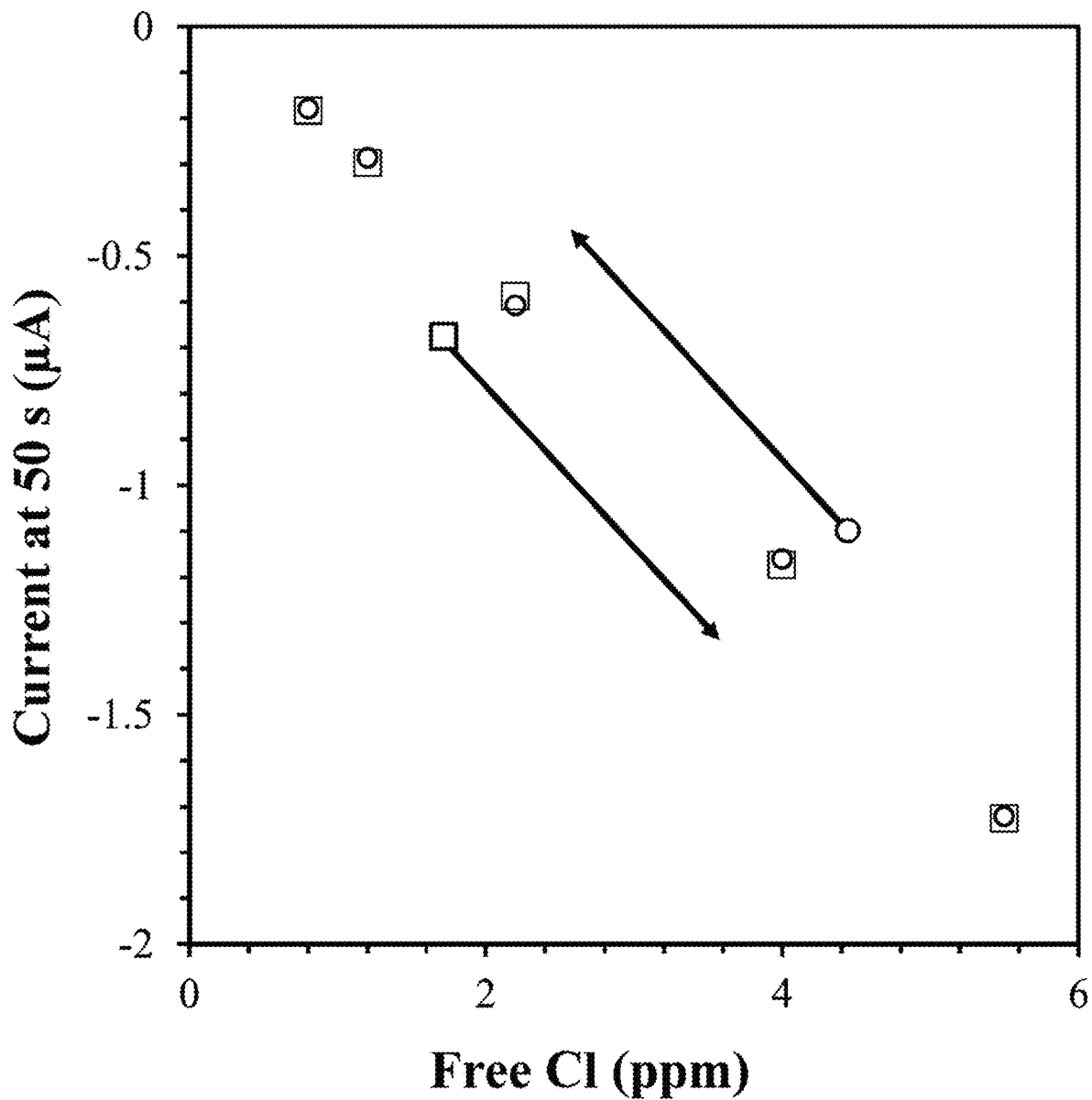
FIG. 8C shows a current response at the 50th second from chronoamperometric response to free chlorine concentrations with respect to increasing (0.8 ppm to 5.5 ppm) and decreasing (5.5 ppm to 0.8 ppm) free chlorine concentrations.

FIGS. 8A to 8C show the hysteresis behavior of the free chlorine sensor. The resolution of the free chlorine sensor was calculated by its hysteresis. The free chlorine concentration was cycled from 0.8 to 5.5, and then again back to 0.8 ppm, as shown in FIG. 8A. FIG. 8B shows the detailed response of the chronoamperometric response from 40 to 50 s to better understand the hysteresis behavior. As shown in FIG. 8C, the average hysteresis of 0.019 µA resulted in a resolution of 0.06 ppm.

Figure 9A:
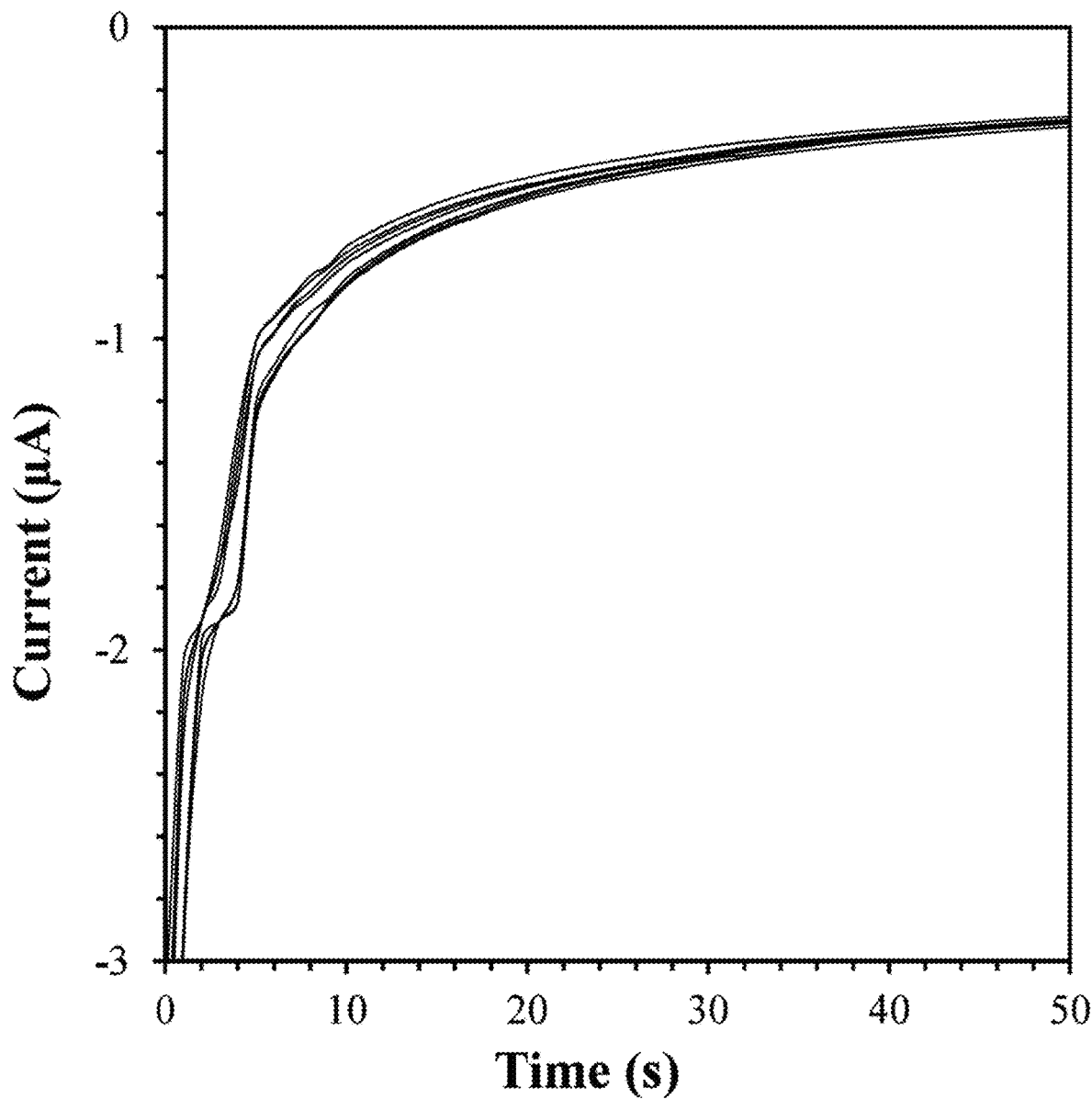
FIG. 9A is a graph of the chronoamperometric response with a fixed concentration of 1.3 ppm free chlorine for several times.
Figure 9B:
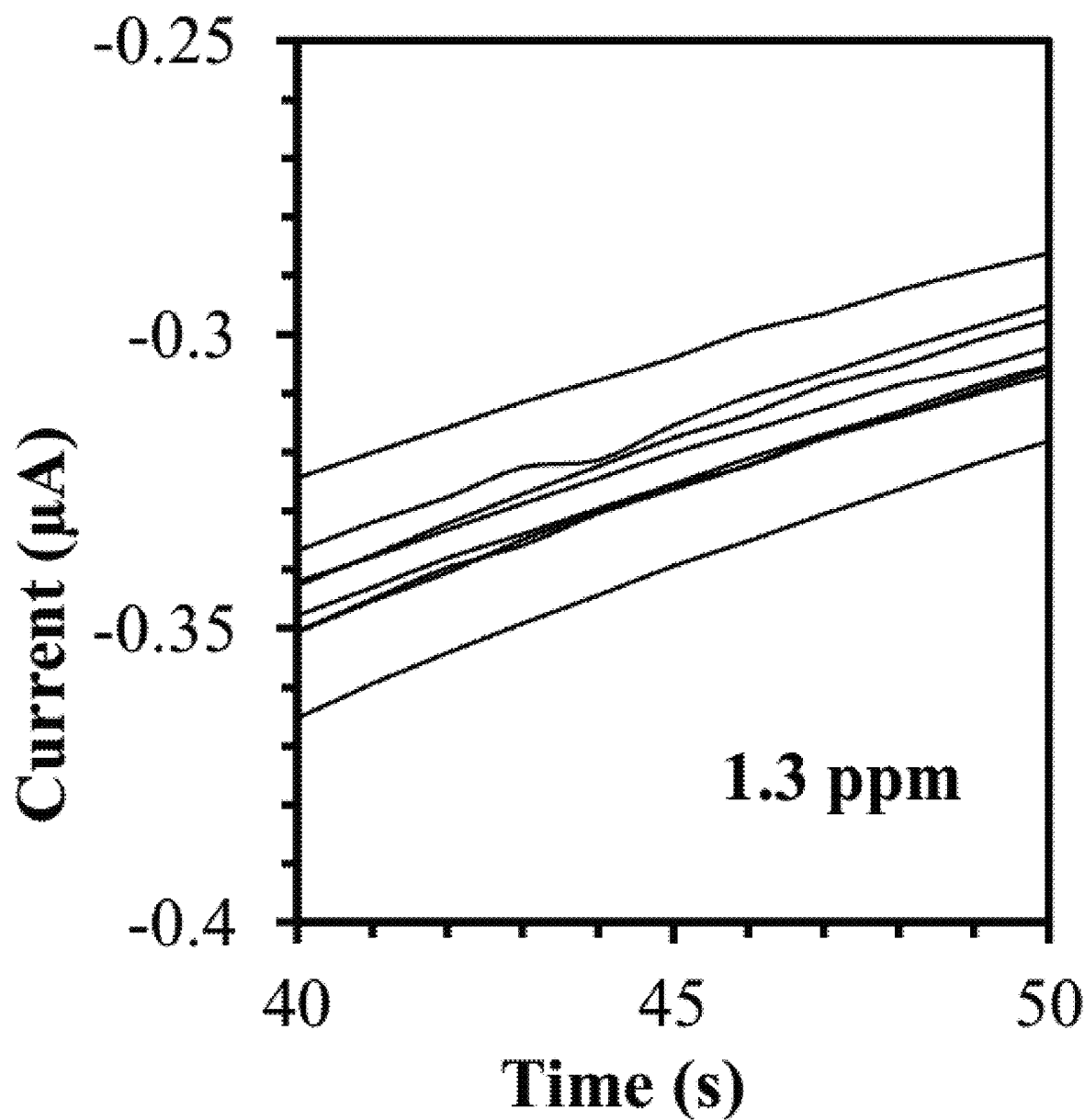
FIG. 9B is an expanded view of a portion of FIG. 9A.

FIG. 9A shows the drift behavior of the free chlorine sensor. The drift behavior was also studied by keeping the free chlorine sensor in 1.3 ppm NaOCl solution for 8 h, and the measurement was done once in every hour, as shown in FIG. 9B. The drift rate was 0.004 µA/h, equivalent to 0.012 ppm/h, which was 5 times lower than the resolution of the sensor.

Figure 10:
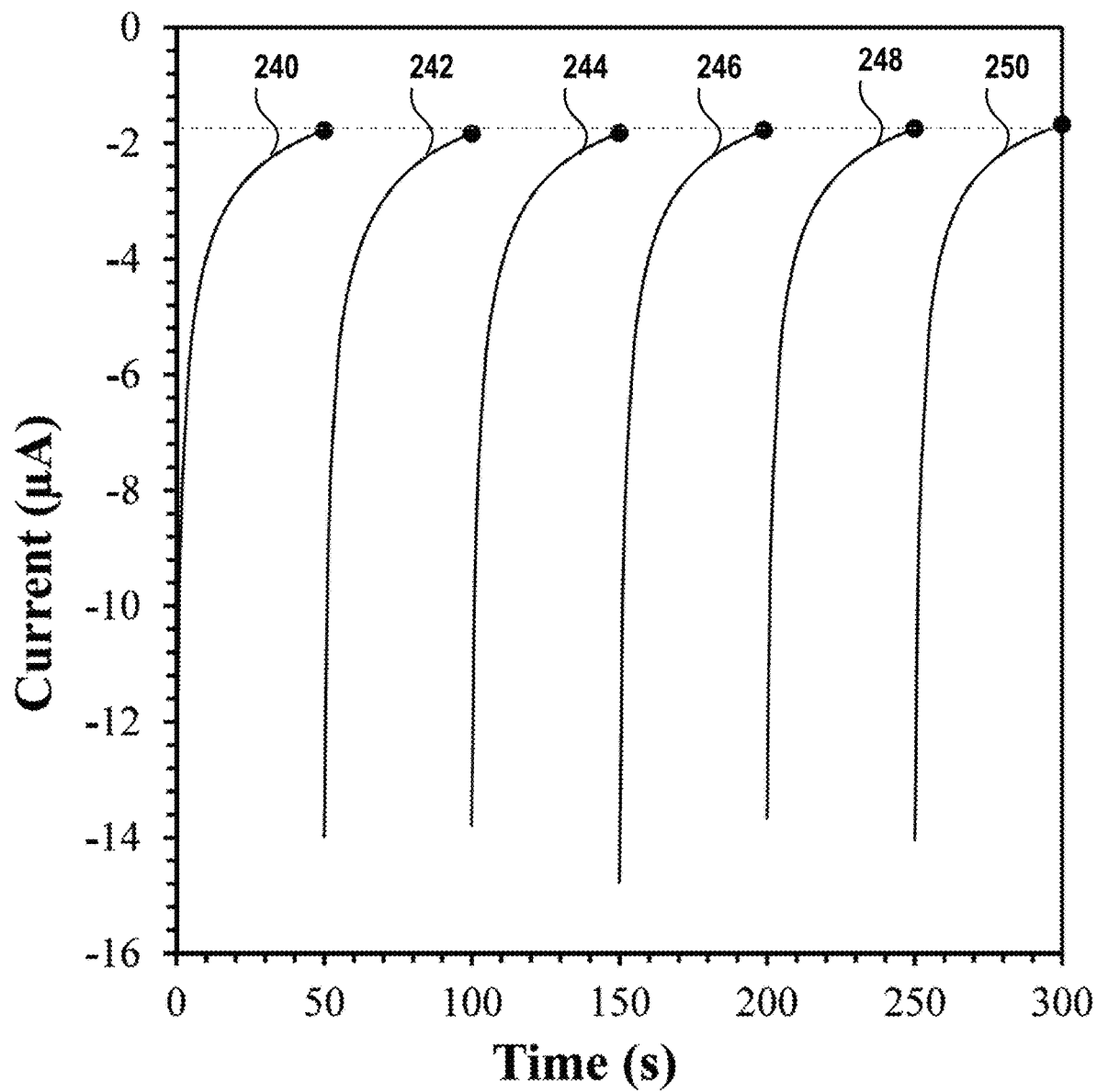
FIG. 10 is a graph of the chronoamperometric response with a fixed concentration of 6 ppm free chlorine with subsequent addition of several interfering ions.

FIG. 10 shows the interference behavior of the free chlorine sensor. Interferences were measured by using sodium nitrate, sodium sulfate, sodium carbonate, sodium bicarbonate, and sodium chloride stock solutions. Free chlorine containing tap and swimming pool waters were tested with the method discussed herein as well as with a commercial colorimeter for comparison. All free chlorine sensing measurements were performed at room temperature (25±2° C.). The selectivity of the free chlorine sensor was studied by recording the sensor response by sequentially adding 10 µL interfering solutions of 7.3 ppm sodium nitrate, 13.5 ppm sodium sulfate, 11.3 ppm sodium carbonate, 14.5 ppm sodium bicarbonate, and 1.8 ppm sodium chloride, respectively, to a 50 mL 0.01 M sodium phosphate (pH 7.4) buffered solution containing 6 ppm free chlorine. The concentrations of the interfering solutions are similar to typical concentrations in real water samples. Illustrated are plots for 6 ppm 240, added $NO_3^-$ 242, added $SO_4^-$ 244, added $CO_3^{2-}$ 246, added $HCO_3^-$ 248, and added $Cl^-$ 250. The interfering solutions had negligible effect on the sensors' response, shown in FIG. 10. After the selectivity test, the free chlorine sensor was still able to show a stable response to the change of free chlorine concentration.

Figure 11A:
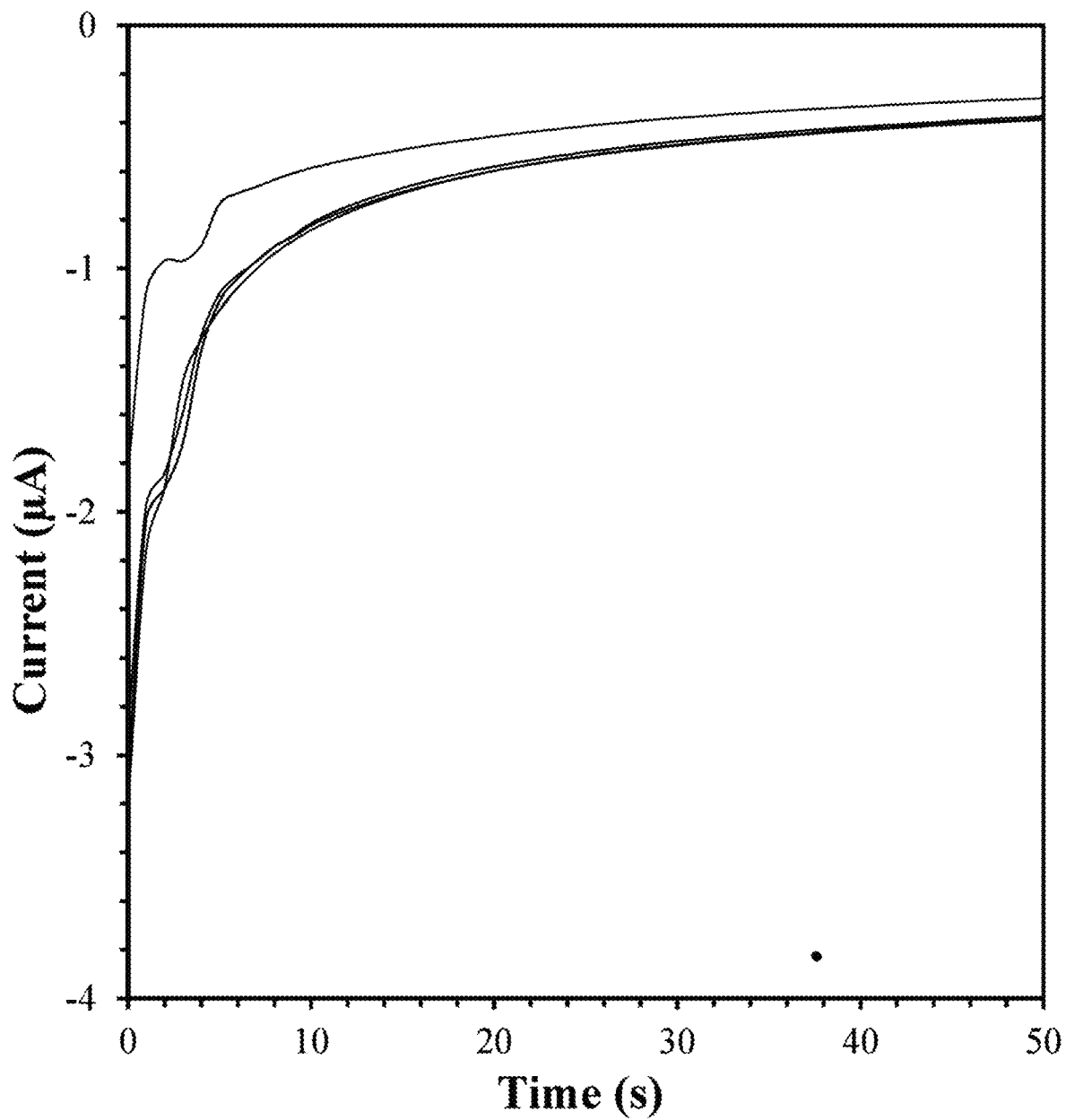
FIG. 11A is a graph of the chronoamperometric response with tap water of fixed concentration of 0.9 ppm free chlorine in different adjusted pH level.

FIG. 11A shows chronoamperometric response to a constant free chlorine concentration of 0.9 ppm in tap water at different adjusted pH level. Typically, the current response of amperometric free chlorine sensors depends on the pH level of the water sample. This is due to the pH dependent dissociation of NaOCl. Therefore, amperometric free chlorine sensors normally require pH compensation. However, some embodiments, the response of the free chlorine sensor did not significantly change with the change in pH level. This is a significant advantage that may allow for simpler free chlorine measurement. The gold thin film based free chlorine sensor of some embodiments, thus, operates reagent-free resulting in lower cost of operation and ease-of-use.

Figure 11B:
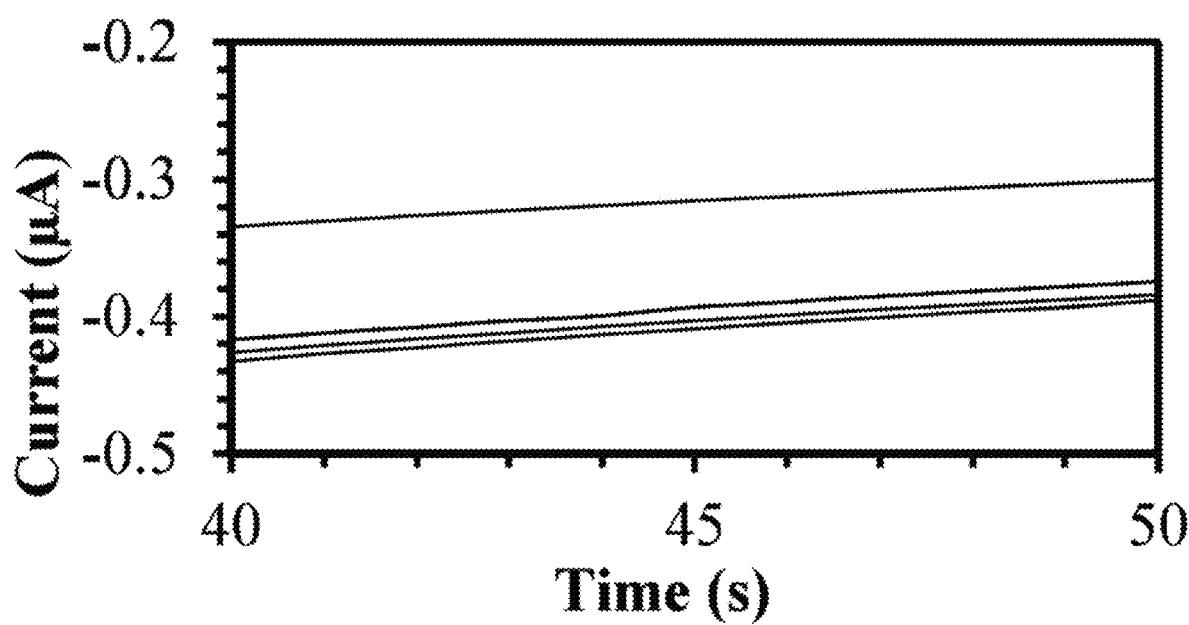
FIG. 11B is an expanded view of a portion of FIG. 11A.
Figure 11C:
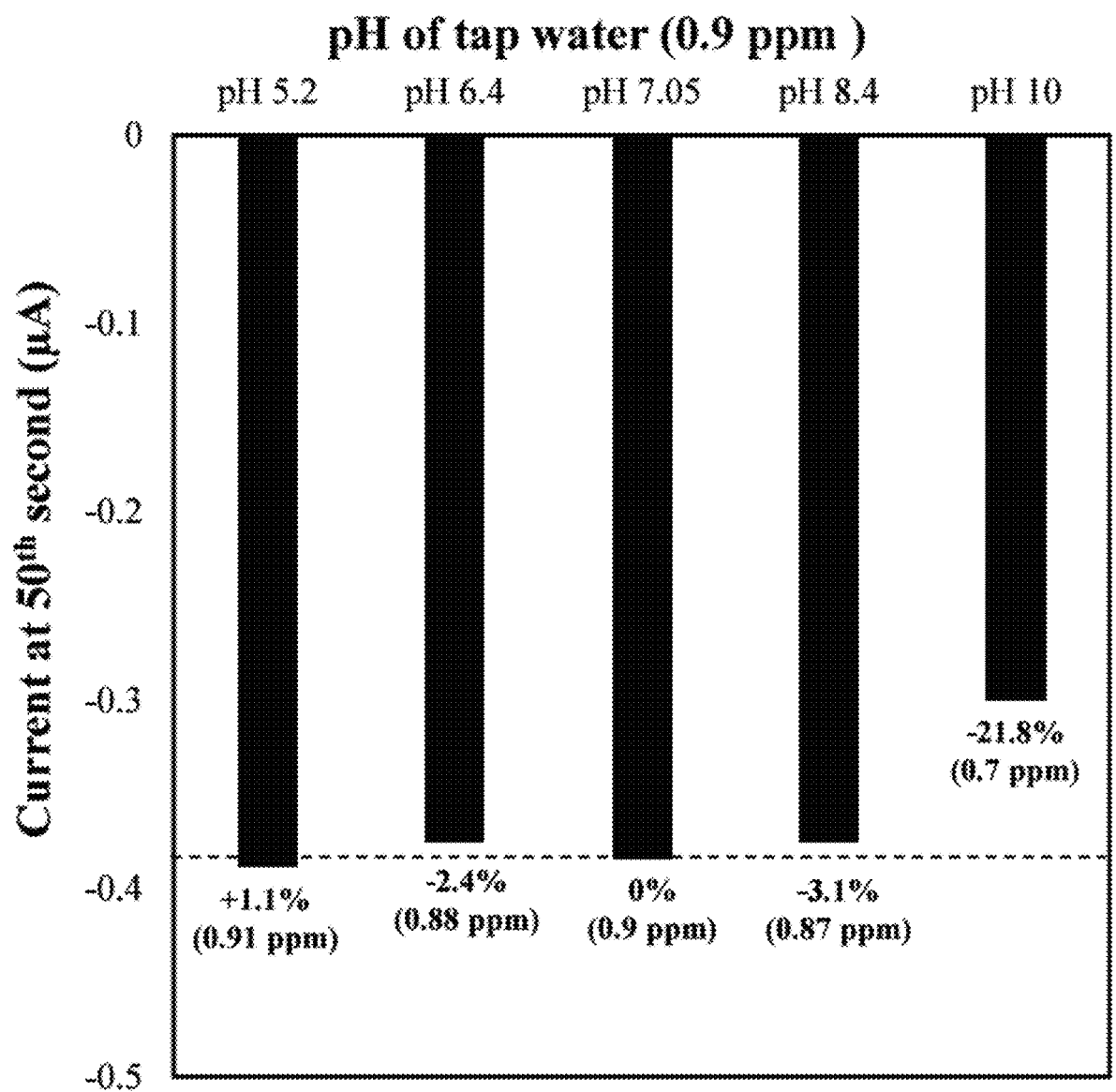
FIG. 11C is a bar chart of a current response at the 50th second from chronoamperometric response to tap water containing 0.9 ppm free chlorine in different adjusted pH level.
Figure 12A:
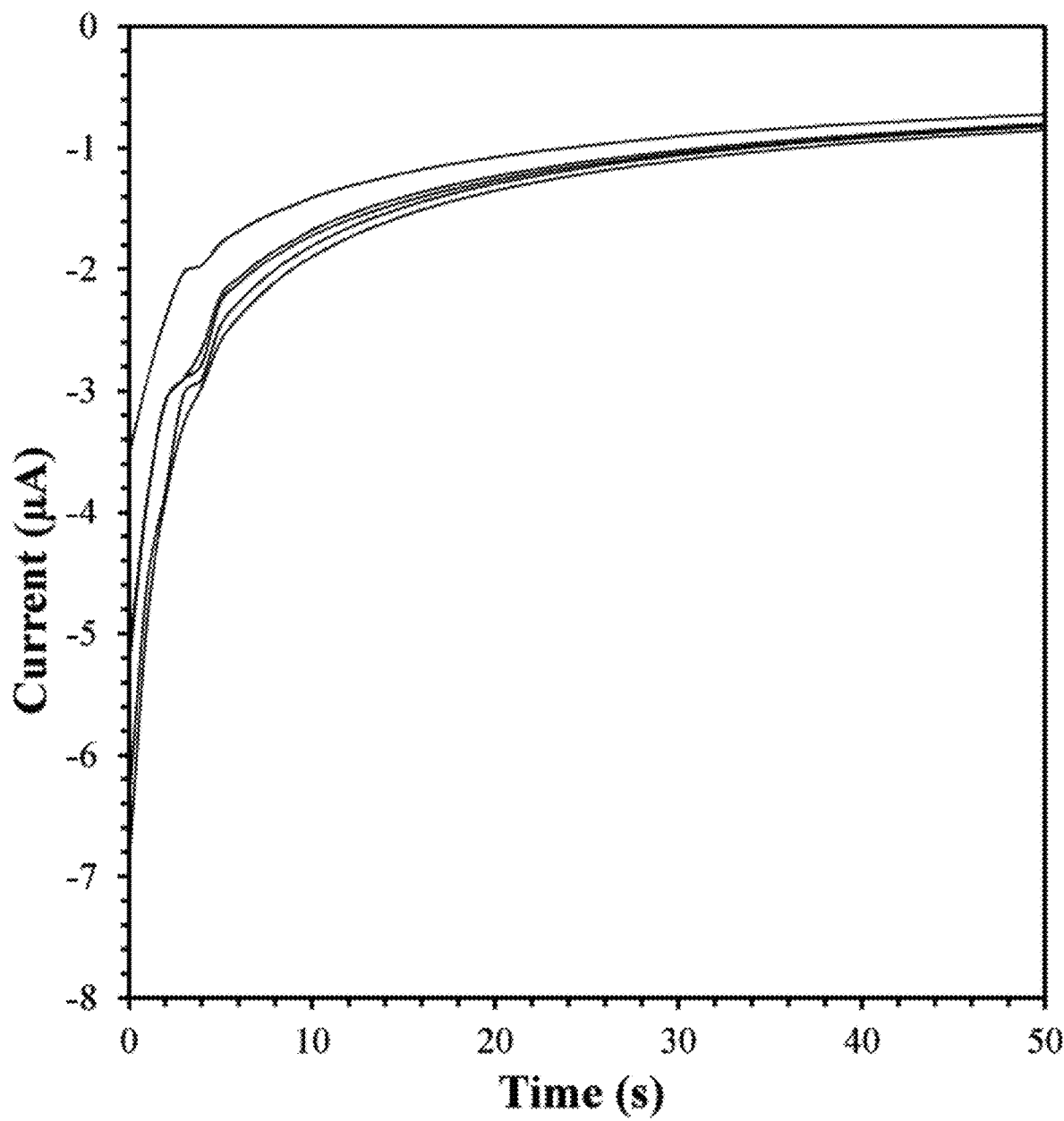
FIG. 12A is a graph of the chronoamperometric response with a water sample of fixed concentration of 2.2 ppm free chlorine in different pH level.
Figure 12B:
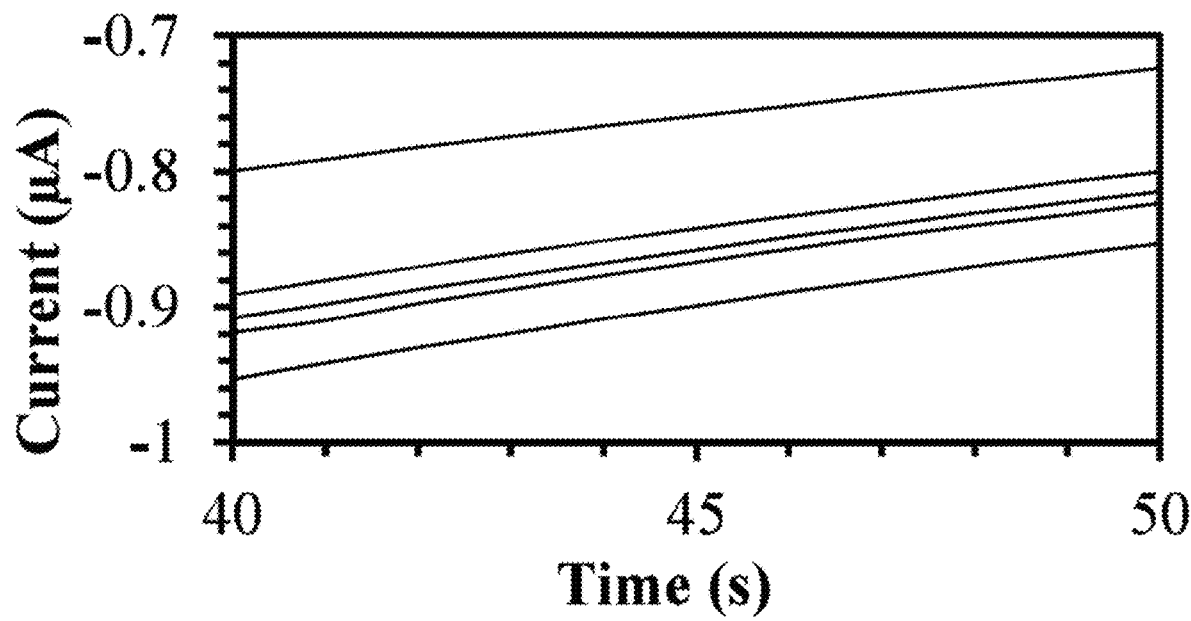
FIG. 12B is an expanded view of a portion of FIG. 12A.
Figure 12C:
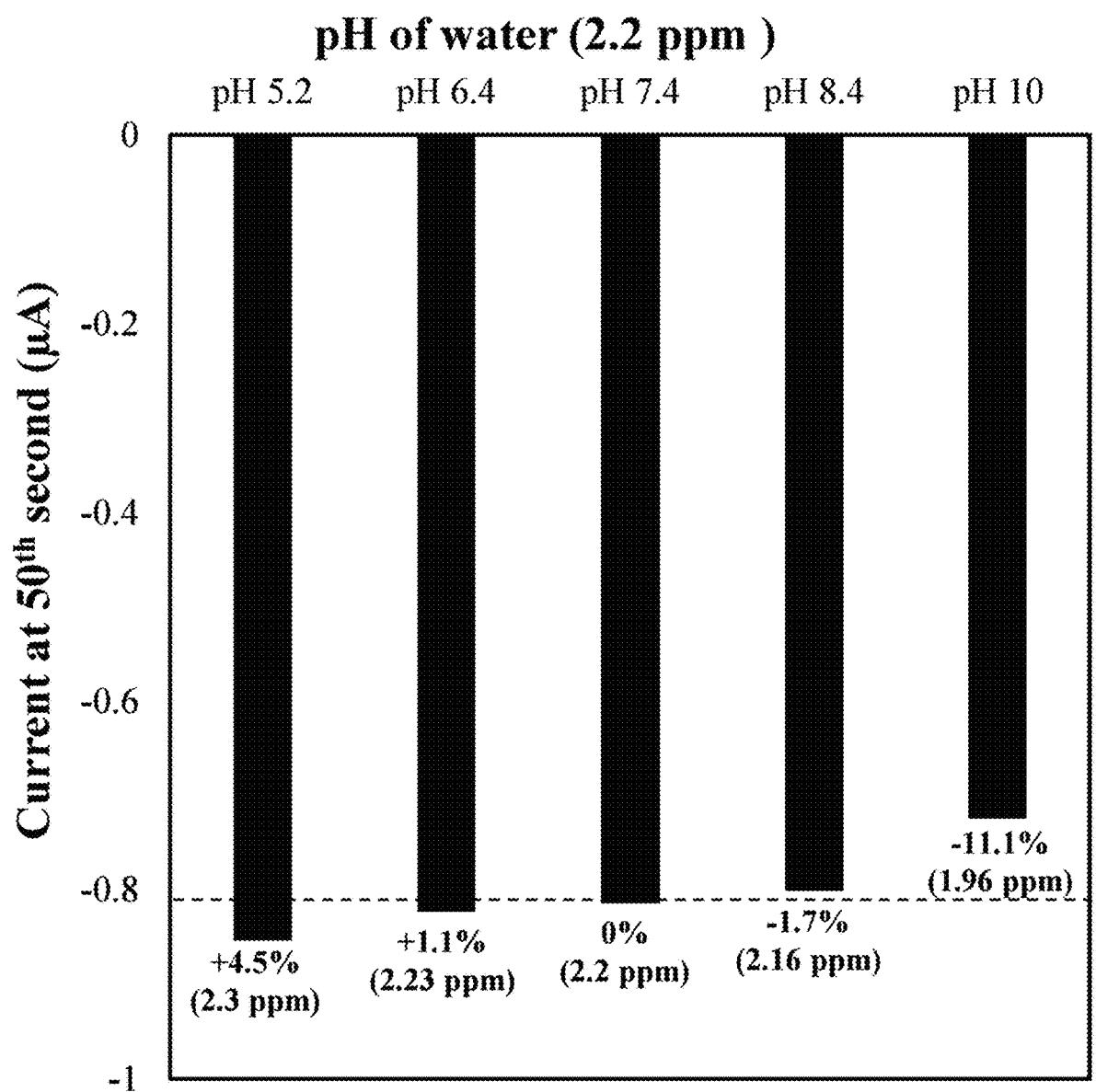
FIG. 12C is a bar chart of a current response at the 50th second from chronoamperometric response to a water sample with 2.2 ppm free chlorine in different pH level.
Figure 13A:
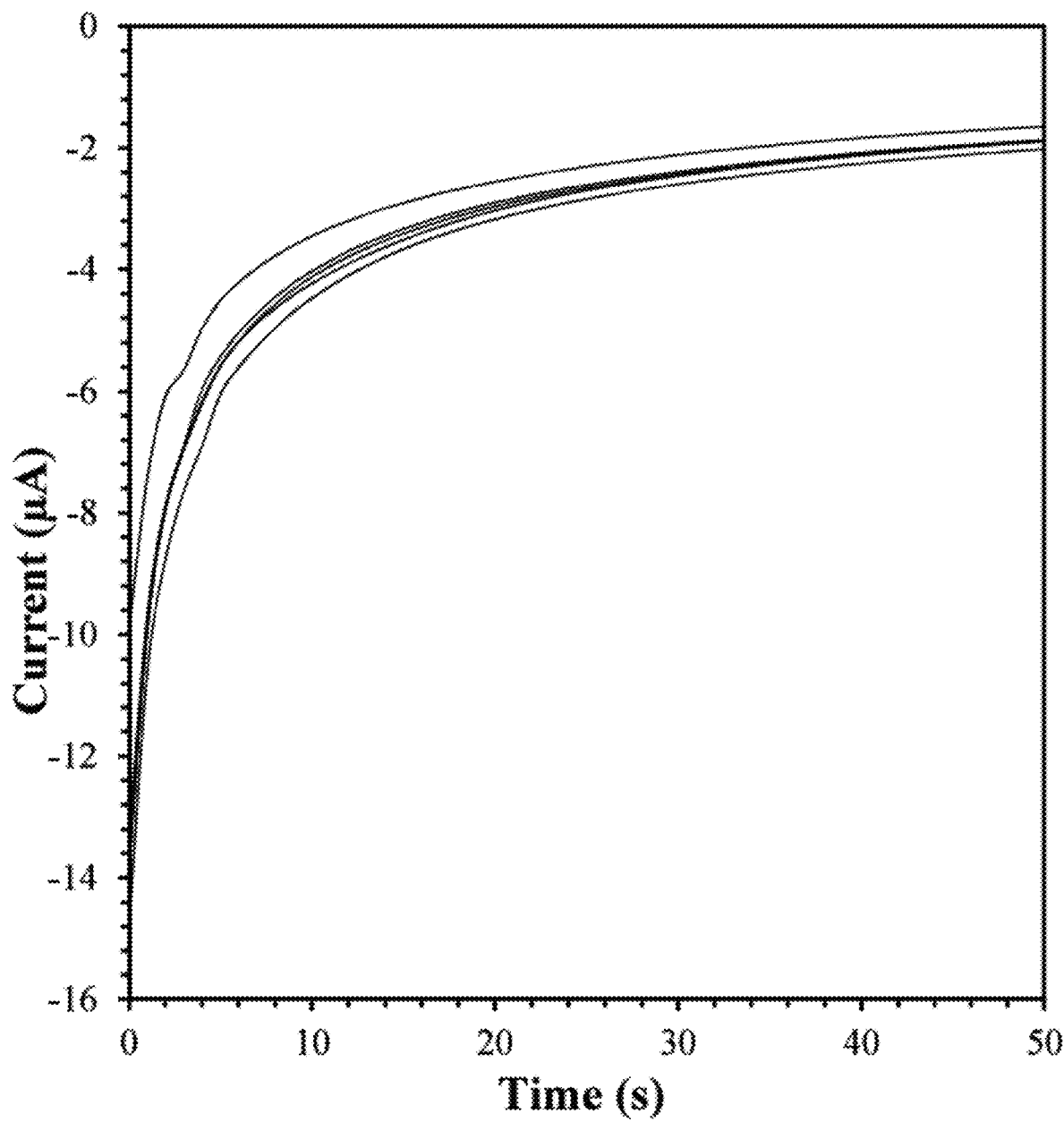
FIG. 13A is a graph of the chronoamperometric response with a water sample of fixed concentration of 5.5 ppm free chlorine in different pH level.
Figure 13B:
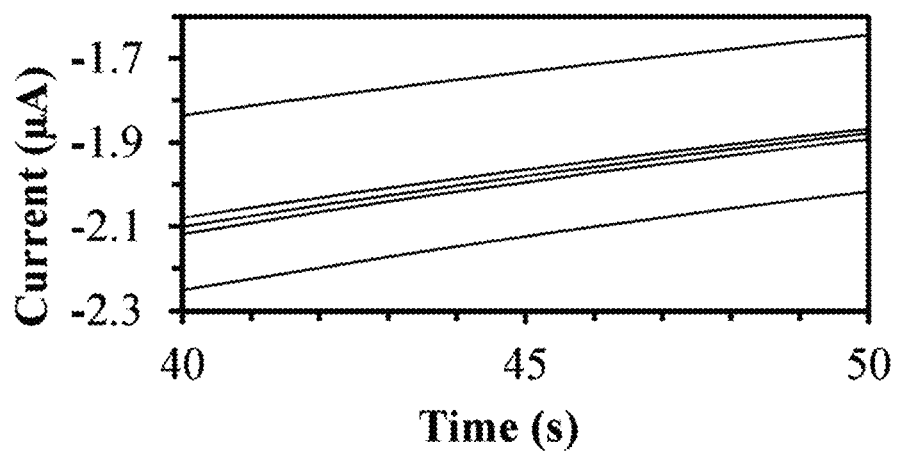
FIG. 13B is an expanded view of a portion of FIG. 13A.
Figure 13C:
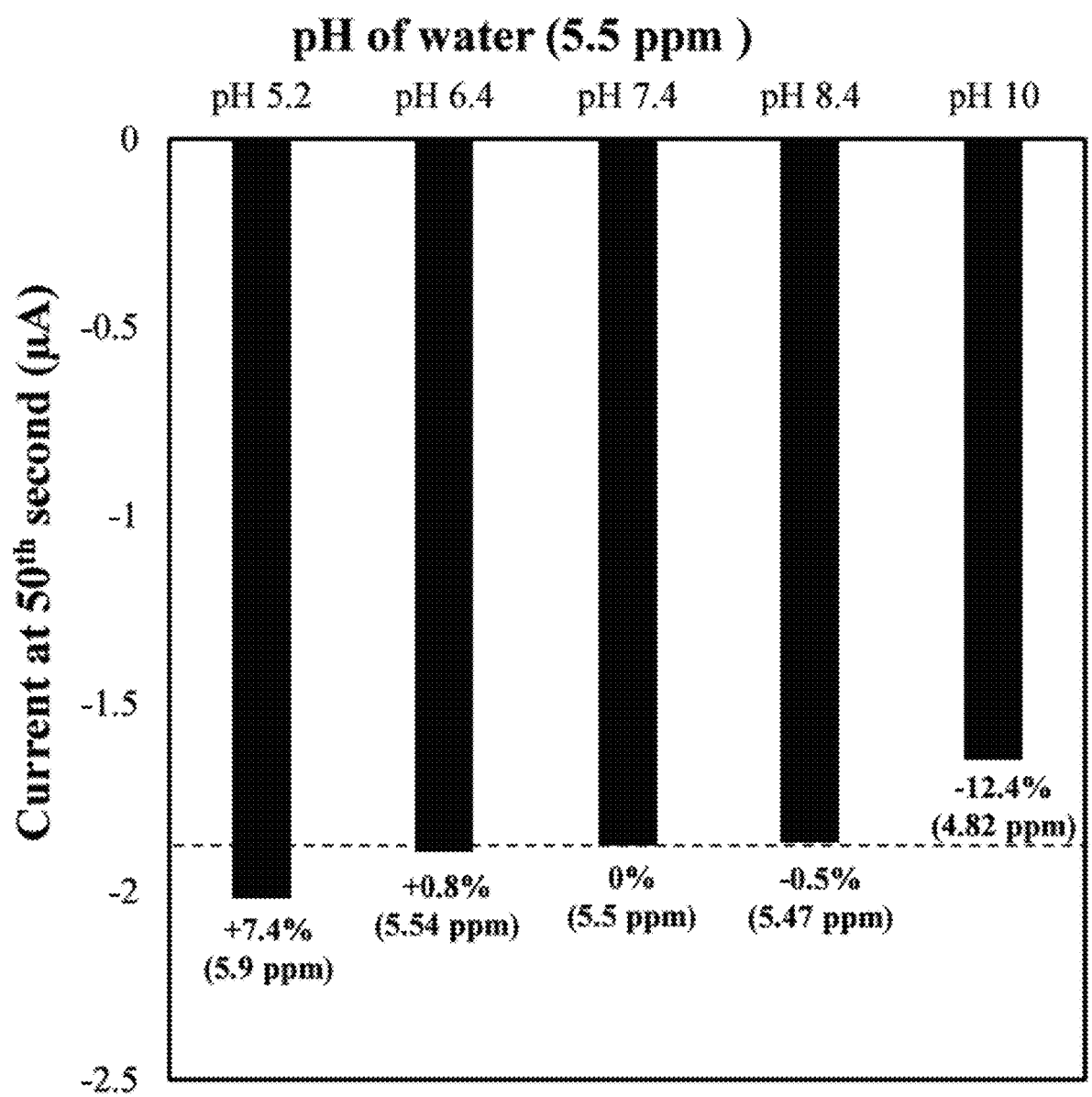
FIG. 13C is a bar chart of a current response at the 50th second from chronoamperometric response to a water sample containing 5.5 ppm free chlorine in different pH level.

FIG. 11B shows detailed chronoamperometric response between 40 s to 50 s, which shows that between pH 5.2 to pH 8.4, the current responses show a very small variation. The upper line in FIG. 11B represents pH 10, while the lower group of lines represent pH 5.2, pH 6.4, pH 7.05, and pH 8.4. FIG. 11C shows the current values at 50th second for each of the pH level in terms of the percentage current as well as absolute ppm values in free chlorine for tap water samples with respect to tap water with pH 7.04. A maximum of −3.1% variation in the free chlorine sensor response was observed between pH 5.2 and pH 8.4, which is lower than the sensitivity tolerance (4%) of this free chlorine sensor. At pH 10, the sensor showed a change of −21.8% in the current response, which is more than the sensitivity tolerance of the free chlorine sensor. However, typical recreational water pH remains within the range of pH 7 to pH 8, therefore, this free chlorine sensor should be able to perform correctly in this pH range.

FIGS. 12A to 12C and 13A to 13C also show pH dependent chronoamperometric response to constant free chlorine concentrations of 2.2 ppm and 5.5 ppm in water samples, respectively, to characterize the sensor performance at medium (2.2 ppm) and high (5.5 ppm) free chlorine concentrations. As shown in FIGS. 12A to 12C and 13A to 13C, the free chlorine sensor response showed maximum variations of 4.5% and 7.4% in their current value, for 2.2 ppm and 5.5 ppm, respectively, between pH 5.2 to pH 8.4. These variations are slightly higher than the sensor's sensitivity tolerance of 4%, but much lower than the variation observed in commercial colorimetric free chlorine sensors (typically more than 10%). Thus, the free chlorine sensor can operate in different concentration ranges without significant variation due to pH level.

Figure 14A:
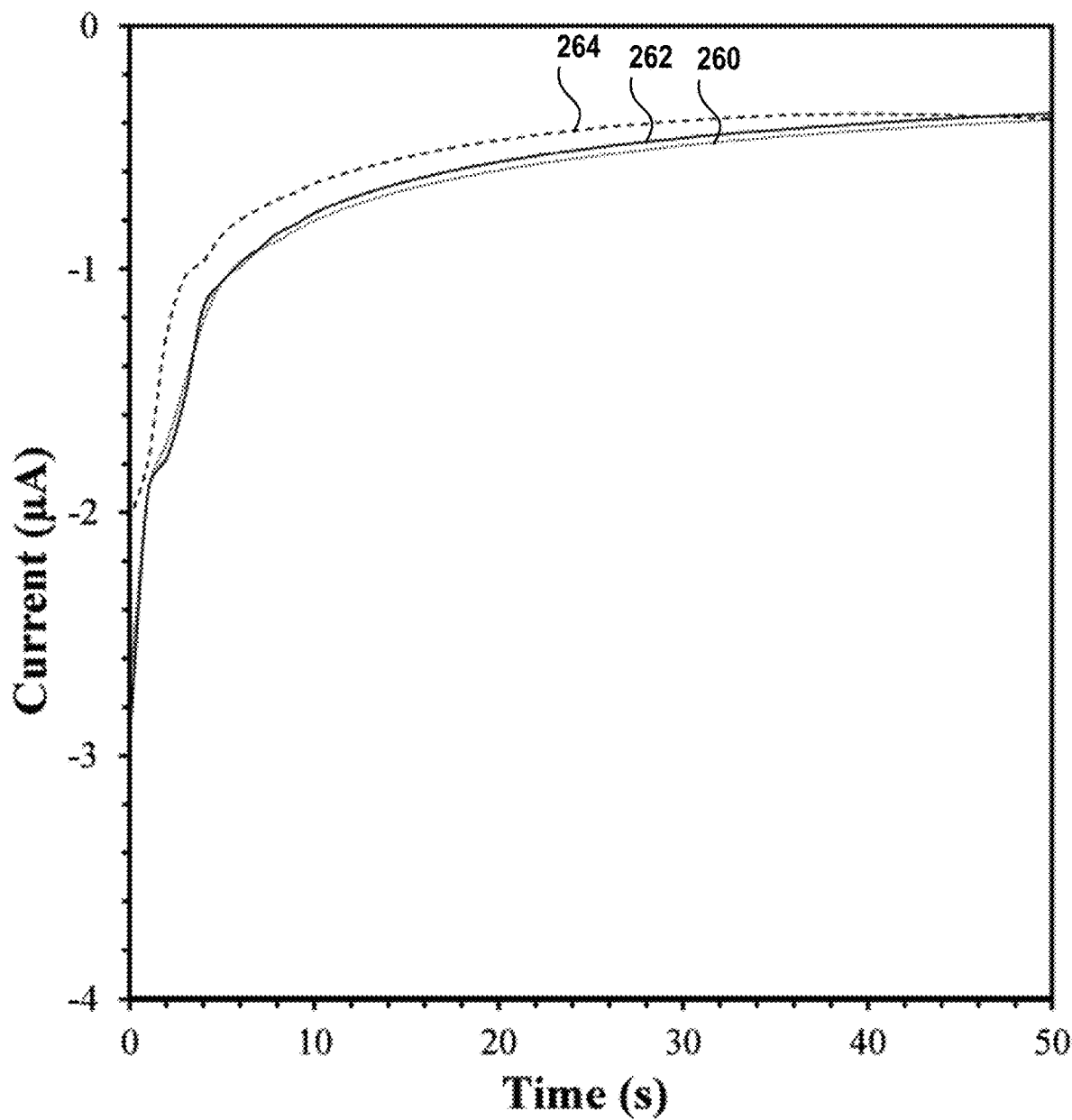
FIG. 14A is a graph of the chronoamperometric response with tap water of fixed concentration of 0.9 ppm free chlorine in different temperature.
Figure 14B:
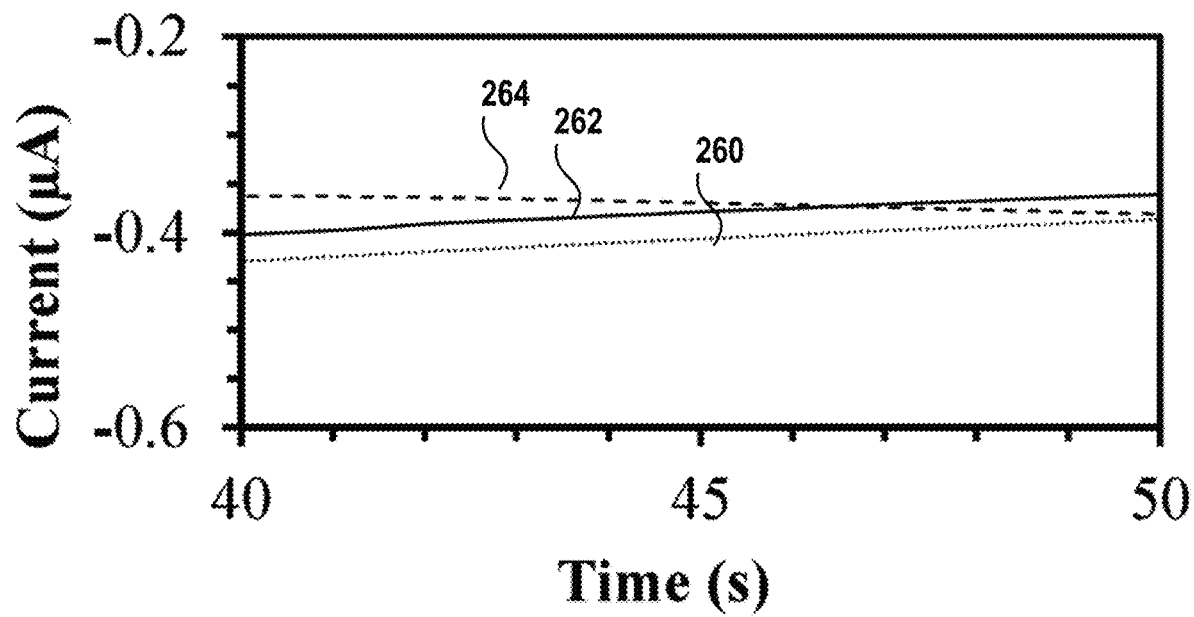
FIG. 14B is an expanded view of a portion of FIG. 14A.
Figure 14C:
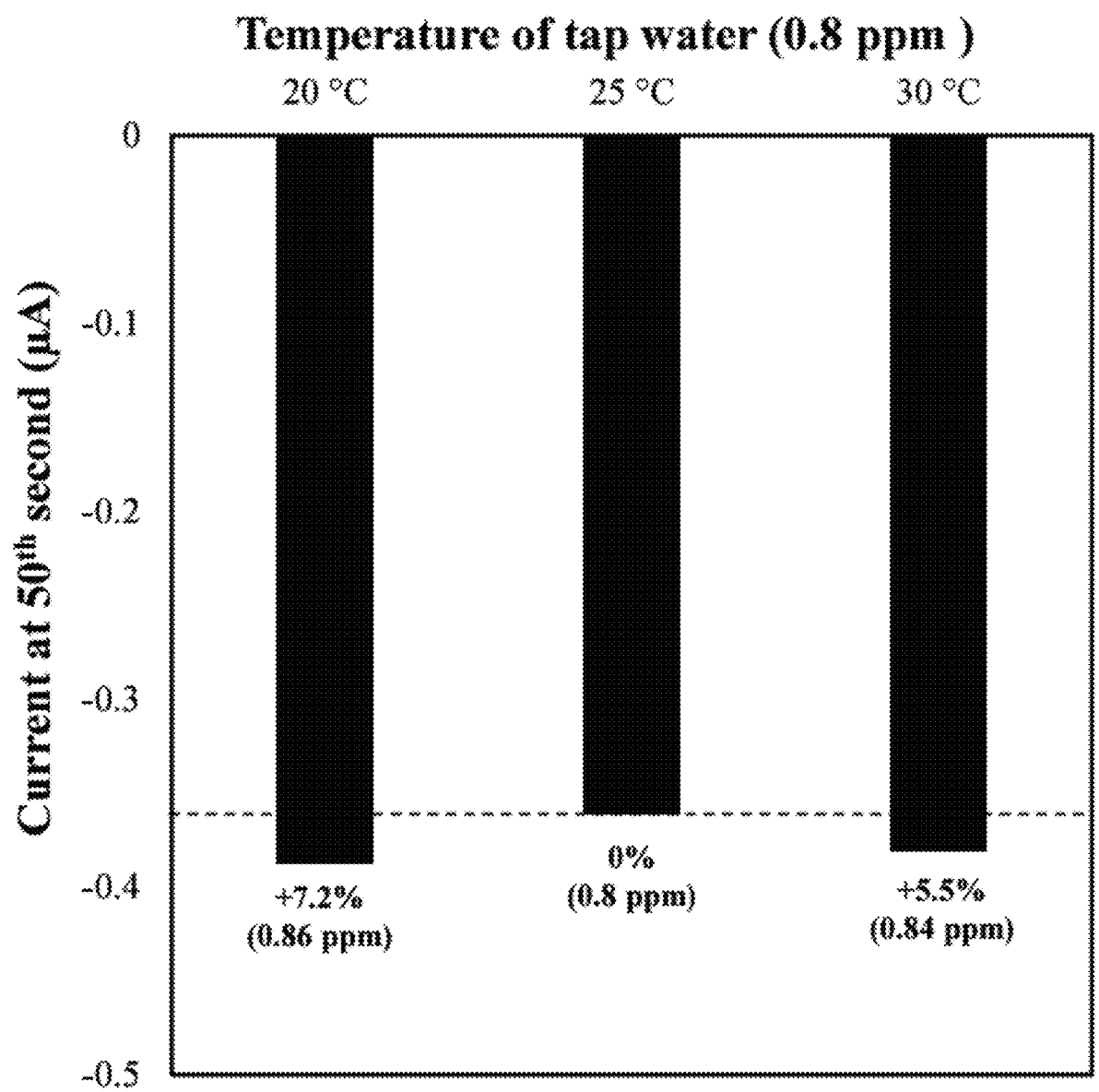
FIG. 14C is a bar chart of a current response at the 50th second from chronoamperometric response to tap water with 0.9 ppm free chlorine in different temperatures.

FIG. 14A shows chronoamperometric response to a constant free chlorine concentration of 0.9 ppm in tap water at different temperatures. Illustrated are plots for tap water at 20 degrees Celsius 260, 25 degrees Celsius 262, and 30 degrees Celsius 264. Typically, the current response of amperometric free chlorine sensors also depends on the temperature, which is due to the temperature dependent dissociation of NaOCl. Therefore, amperometric free chlorine sensors normally require temperature compensation. However, in some embodiments of the present disclosure, the response of the free chlorine sensor did not significantly change with the change in temperature. This may be another significant advantage that may allow for simpler free chlorine measurement. FIG. 14B shows detailed chronoamperometric response between 40 s to 50 s, which shows that between temperatures 20 to 30° C., the current responses show a very small variation at 50th second. FIG. 14C shows the current values at 50th second for each of the temperatures in terms of the percentage current as well as absolute ppm values in free chlorine for tap water samples with respect to tap water at temperature 25° C. A maximum of 7.2% variation in the free chlorine sensor response was observed, which is slightly higher than the sensitivity tolerance (4%) of this free chlorine sensor. However, typical recreational water temperature remains within the range of 24 to 29° C., therefore, this free chlorine sensor should be able to perform correctly in this temperature range.

While the above description provides examples of one or more apparatus, methods, or systems, it will be appreciated that other apparatus, methods, or systems may be within the scope of the claims as interpreted by one of skill in the art.

We claim:

1. An electrochemical sensor array for detecting analytes in water, comprising:
   a) a frame;
   b) a plurality of sensor electrodes each mounted to the frame, including:
      i) a free chlorine working electrode including a gold thin film and having a free chlorine sensing surface to be exposed to the water; and
      ii) a reference and counter electrode including a silver thin film and a silver and silver chloride layer and having a reference sensing surface to be exposed to the water, and
   wherein the plurality of electrodes further comprises a total chlorine electrode including a carbon thin film and a total chlorine sensing reagent layer and having a total chlorine sensing surface to be exposed to the water, the total chlorine sensing reagent layer including amine-containing compounds and a binding polymer.

2. The electrochemical sensor array of claim 1, wherein the gold thin film includes a first end having the free chlorine sensing surface and a second end to be coupled to readout circuitry, with a passivation layer on the gold thin film between the first end and the second end.

3. The electrochemical sensor array of claim 2, wherein the passivation layer covers the gold thin film apart from the free chlorine sensing surface and a surface to be coupled to the readout circuitry.

4. The electrochemical sensor array of claim 1, wherein the reference sensing surface is a surface of the silver and silver chloride layer, and the silver and silver chloride layer is on a first end of the silver thin film and the silver thin film includes a second end to be coupled to readout circuitry, with a passivation layer on the silver thin film between the first end and the second end.

5. The electrochemical sensor array of claim 4, wherein the passivation layer covers the silver thin film apart from a first surface covered by the silver/silver chloride layer and a second surface to be coupled to the readout circuitry.

6. The electrochemical sensor array of claim 1, wherein the total chlorine sensing surface is a surface of the total chlorine sensing reagent layer, and the total chlorine sensing reagent layer is on a first end of the carbon thin film and the carbon thin film includes a second end to be coupled to readout circuitry, with a passivation layer on the carbon thin film between the first and second ends.

7. The electrochemical sensor array of claim 6, wherein the passivation layer covers the carbon thin film apart from a first surface covered by the total chlorine sensing reagent layer and a second surface to be coupled to the readout circuitry.

8. The electrochemical sensor array of claim 1, wherein the plurality of electrodes further comprises an alkalinity electrode including a carbon thin film and an alkalinity sensing reagent layer having an alkalinity sensing surface to be exposed to the water, the alkalinity sensing reagent layer including manganese perchlorate and a binding polymer.

9. The electrochemical sensor array of claim 8, wherein the alkalinity sensing surface is a surface of the alkalinity sensing reagent layer, and the alkalinity sensing reagent layer is on a first end of the carbon thin film and the carbon thin film includes a second end to be coupled to readout circuitry, with a passivation layer on the carbon thin film between the first and second ends.

10. The electrochemical sensor array of claim 9, wherein the passivation layer covers the carbon thin film apart from a first surface covered by the alkalinity sensing reagent layer and a second surface to be coupled to the readout circuitry.

11. The electrochemical sensor array of claim 1, wherein the frame includes a common plate, and each of the plurality of electrodes is mounted to the common plate.

12. An electrochemical sensor array for detecting analytes in water, comprising:
   a) a frame;
   b) a plurality of sensor electrodes each mounted to the frame, including:
      i) a free chlorine working electrode including a gold thin film and having a free chlorine sensing surface to be exposed to the water; and
      ii) a reference and counter electrode including a silver thin film and a silver and silver chloride layer and having a reference sensing surface to be exposed to the water, and
   wherein the plurality of electrodes further comprises a pH electrode including a platinum and/or tantalum thin film and having a pH sensing surface to be exposed to the water, and
   wherein the pH sensing surface is a surface of an oxide layer of the platinum and/or tantalum thin film, and the oxide layer is on a first end of the platinum and/or tantalum thin film and the platinum and/or tantalum thin film includes a second end to be coupled to readout circuitry, with a passivation layer on the platinum and/or tantalum thin film between the first and second ends.

13. The electrochemical sensor array of claim 12, wherein the passivation layer covers the platinum and/or tantalum thin film apart from the oxide layer and a surface to be coupled to the readout circuitry.

14. A method of manufacturing an electrochemical sensor array for detecting analytes in water, comprising:
   a) forming a free chlorine electrode, including forming a gold thin film on a first base layer;
   b) forming a reference electrode, including forming a silver thin film on a second base layer and applying a silver and silver chloride paste to a portion of the silver thin film; and
   c) arranging the free chlorine electrode and the reference electrode on a common frame.

15. The method of claim 14, wherein arranging the free chlorine electrode and the reference electrode on a common frame includes removing one of the free chlorine electrode and the reference electrode from a second frame on which it was formed and transferring the one of the free chlorine electrode and the reference electrode to the common frame.

16. The method of claim 15, wherein removing the one of the free chlorine electrode and the reference electrode includes cutting the one of the free chlorine electrode and the reference electrode free of the second frame and transferring it to the common frame.

17. The method of claim 16, wherein:
 a) forming the free chlorine electrode includes:
  i) arranging the first base layer on the common frame,
  ii) applying a first chromium adhesion layer on the first base layer via a first sputtering process,
  iii) applying the gold thin film on the chromium adhesion layer via a second sputtering process, and
  iv) applying a first passivation layer to the gold thin film between a first end and a second end of the gold thin film;
 b) forming the reference electrode includes:
  i) arranging the second base layer on the second frame,
  ii) applying a second chromium adhesion layer on the second base layer via a third sputtering process,
  iii) applying the silver thin film on the second chromium adhesion layer via a fourth sputtering process, and
  iv) applying a second passivation layer to the silver thin film between a first end and a second end of the silver thin film, and
  v) applying the silver and silver chloride paste to the portion of the silver thin film at the first end.

18. A method of sensing free chlorine using an electrochemical sensor array for detecting analytes in water, the electrochemical sensor array comprising:
 a) a frame;
 b) a plurality of sensor electrodes each mounted to the frame, including:
  i) a free chlorine working electrode including a gold thin film and having a free chlorine sensing surface to be exposed to the water; and
  ii) a reference and counter electrode including a silver thin film and a silver and silver chloride layer and having a reference sensing surface to be exposed to the water, and
the method comprising:
 a) immersing the free chlorine electrode in the water;
 b) immersing the reference electrode in the water along with the free chlorine electrode, the reference electrode also functioning as a counter electrode;
 c) joining the free chlorine electrode and the reference electrode via readout circuitry, the readout circuitry including a potentiostat;
 d) applying 0 volts voltage potential difference between the free chlorine electrode and the reference electrode;
 e) measuring and recording the current response from the free chlorine electrode for a predetermined time while the free chlorine electrode and the reference electrode are immersed in the water during step (d); and
 f) comparing the current at the predetermined time with a pre-calculated calibration plot to measure the free chlorine concentration.

\* \* \* \* \*